United States Patent
Grant et al.

(10) Patent No.: US 8,357,165 B2
(45) Date of Patent: Jan. 22, 2013

(54) REFERENCE ARRAY MOUNTING BRACKET FOR USE WITH A COMPUTER ASSISTED ORTHOPAEDIC SURGERY SYSTEM

(75) Inventors: Stuart Grant, Warsaw, IN (US); Darren L. Deffenbaugh, Winona Lake, IN (US)

(73) Assignee: DePuy Products, Inc., Warsaw, IN (US)

( * ) Notice: Subject to any disclaimer, the term of this patent is extended or adjusted under 35 U.S.C. 154(b) by 999 days.

(21) Appl. No.: 11/946,445

(22) Filed: Nov. 28, 2007

(65) Prior Publication Data
US 2008/0177173 A1 Jul. 24, 2008

Related U.S. Application Data

(60) Provisional application No. 60/871,593, filed on Dec. 22, 2006.

(51) Int. Cl.
*A61F 2/46* (2006.01)
(52) U.S. Cl. .................................................. 606/86 R
(58) Field of Classification Search .............. 606/96, 606/86 R
See application file for complete search history.

(56) References Cited

U.S. PATENT DOCUMENTS

| 6,122,541 | A * | 9/2000 | Cosman et al. ............. 600/426 |
| 6,298,262 | B1 | 10/2001 | Franck et al. |
| 6,856,828 | B2 * | 2/2005 | Cossette et al. ............. 600/429 |
| 6,859,660 | B2 | 2/2005 | Vilsmeier |
| 6,932,823 | B2 | 8/2005 | Grimm et al. |
| 7,764,985 | B2 * | 7/2010 | McCombs et al. ............. 600/429 |
| 7,862,570 | B2 * | 1/2011 | Russell et al. ................... 606/87 |
| 2001/0007918 | A1 * | 7/2001 | Vilsmeier et al. ............. 600/426 |
| 2004/0054489 | A1 * | 3/2004 | Moctezuma De La Barrera et al. ............................ 702/105 |
| 2004/0167391 | A1 * | 8/2004 | Solar et al. ..................... 600/411 |
| 2005/0049485 | A1 | 3/2005 | Harmon et al. |
| 2005/0049486 | A1 * | 3/2005 | Urquhart et al. ............. 600/429 |
| 2005/0055035 | A1 | 3/2005 | Cosman et al. |
| 2005/0149050 | A1 | 7/2005 | Stifter et al. |
| 2006/0052792 | A1 * | 3/2006 | Boettiger et al. ............... 606/88 |

FOREIGN PATENT DOCUMENTS

| DE | 103 09 500.4 | * | 2/2003 |
| EP | 1523950 | | 4/2005 |
| WO | 0396870 | | 11/2003 |
| WO | 03096870 | | 11/2003 |
| WO | 2006050010 | | 5/2006 |

OTHER PUBLICATIONS

European Search Report for European Patent Application No. 07255015.5, Apr. 25, 2008, 7 pgs.

* cited by examiner

*Primary Examiner* — Kevin T Truong
*Assistant Examiner* — David Bates
(74) *Attorney, Agent, or Firm* — Barnes & Thornburg LLP

(57) ABSTRACT

A mounting bracket for use with a reference array of a computer assisted surgery system includes a base and an arcuate support frame coupled to the base. The base is configured to be secured to a bone of a patient. The arcuate support frame includes a plurality of mounts. Each mount is configured to receive a mounting end of the reference array. In some embodiments, the arcuate support frame may be pivotable with respect to the base. Additionally, in some embodiments, the arcuate support frame may be movable about an arc defined by the arcuate support frame.

18 Claims, 17 Drawing Sheets

REFERENCE ARRAY MOUNTING BRACKET FOR USE WITH A COMPUTER ASSISTED ORTHOPAEDIC SURGERY SYSTEM

This patent application claims priority to and the benefit of U.S. Provisional Patent Application Ser. No. 60/871,593 entitled "REFERENCE ARRAY MOUNTING BRACKET FOR USE WITH A COMPUTER ASSISTED ORTHOPAEDIC SURGERY SYSTEM," which was filed on Dec. 22, 2006 by Daren L. Deffenbaugh et al., the entirety of each of which is expressly incorporated herein by reference.

TECHNICAL FIELD

The present disclosure relates generally to computer assisted orthopaedic surgery systems, and more particularly, to reference arrays used with such systems.

BACKGROUND

There is an increasing adoption of minimally invasive orthopaedic procedures. Because such surgical procedures generally restrict the surgeon's ability to see the operative area, surgeons are increasingly relying on computer systems, such as computer assisted orthopaedic surgery (CAOS) systems, to assist in the surgical operation.

Computer assisted orthopaedic surgery (CAOS) systems assist surgeons in the performance of orthopaedic surgical procedures by, for example, displaying images illustrating surgical steps of the surgical procedure being performed and rendered images of the relevant bones of the patient. In particular, computer assisted orthopaedic surgery (CAOS) systems provide surgical navigation to the surgeon by displaying the relative position of the relevant bones of the patient throughout the orthopaedic surgical procedure. To do so, a reference array is typically coupled to the relevant bone of the patient and registered with the computer assisted orthopaedic surgery system. In computer assisted orthopaedic surgery (CAOS) systems using optical tracking, the reference arrays provide an optical signal to a camera of the computer assisted orthopaedic surgery (CAOS) systems. To provide accurate navigation, the camera must have continuous line-of-sight to the reference array. However, in some orthopaedic surgical procedures, such as a Total Shoulder Arthroplasty surgical procedure, the reference array may become obscured from the view of the camera by the body of the patient.

SUMMARY

According to one aspect, a reference array assembly for use with a computer assisted surgery system may include a reference array and a mounting bracket. The reference array may include a mounting end. The mounting bracket may include a base and an arcuate support frame. The base may be configured to be coupled to a bone of a patient. For example, the base may be configured to be coupled to the bone of the patient via use of a number of bone screws, bone nails, bone pins, and/or other securing members. In some embodiments, the base may be positionable along a length of the bone screws. In such embodiments, the base may include a securing member, such as a screw, configured to engage at least one of the bone screws to secure the based in a fixed position relative to the bone screws.

The arcuate support frame may be coupled to the base. The arcuate support frame may include a plurality of mounts. In some embodiments, the mounts may be evenly located on the arcuate support frame with respect to each other. Each of the mounts may be configured to receive a mounting end of the reference array. For example, each of the mounts of the arcuate support frame may include an aperture configured to receive a guide pin of the reference array. Additionally, each of the mounts may include a planar top surface configured to confront a planar bottom surface of the mounting end of the reference array when the reference array is coupled to the arcuate support frame. Alternatively, each of the mounts may include a curved top surface configured to confront a curved bottom surface of the mounting end of the reference array when the reference array is coupled to the arcuate support frame.

In some embodiments, the arcuate support frame may include a rail defined on a top surface. The rail may be centrally located or may be located toward one of the lateral sides of the arcuate support frame. In such embodiments, the mounting end of the reference array may include a recess configured to receive the rail when the reference array is coupled to the arcuate support frame. Additionally, in some embodiments, each of the mounts may be embodied as or otherwise include a recess defined in a bottom surface of the arcuate support frame. Additionally or alternatively, each of the mounts may be embodied as a first recess and a second recess defined in a first and second lateral side of the arcuate support frame, respectively. The first recess may include a geometric shape that is different from the geometric shape of the second recess. For example, the first recess may have a rectangular shape while the second recess has a triangular shape. Alternatively, the first recess and second recess may have similar geometric shapes, but of different sizes. For example, the first recess may have rectangular shape that is smaller than the rectangular shape of the second recess. In such embodiments, the mounting end of the arcuate support frame may include a first protrusion and a second protrusion. The first recess may be configured to receive the first protrusion and the second recess may be configured to receive the second protrusion.

The arcuate support frame may subtend an angle from about 90 degrees to about 180 degrees. For example, in some embodiments, the arcuate support frame may subtend an angle of about 120 degrees. In another embodiment, the arcuate support frame may subtend an angle from about 150. Additionally, the arcuate support frame may include a rib support defined on a top surface and/or a bottom surface. For example, the arcuate support frame may include an outer curved surface and an inner curved surface The rib support may be defined on the outer curved surface and/or the inner curved surface between at least two of the mounts to thereby provide additional support to the arcuate support frame. The arcuate support frame may have a cross-section of any shape. For example, in some embodiments, the arcuate support frame has a circular or oval cross-section.

In some embodiments, the arcuate support frame is pivotably coupled to the base such that the arcuate support frame may be pivoted with respect to the base. In such embodiments, the mounting bracket may include an angle sensor configured to generate data indicative of an angle defined between the base and the arcuate support frame. In another embodiment, the arcuate support frame is movable with respect to the base about an arcuate path defined by the arcuate support frame. In such embodiments, the mounting bracket may include a distance sensor configured to generate data indicative of the distance of the arcuate support frame along the arcuate path with respect to a predetermined position of the arcuate support frame. Additionally, in some embodiments, the mounting bracket may include an additional reference array coupled to the base.

According to another aspect, a method for operating a computer assisted orthopaedic surgery system may include coupling a mounting bracket to a bone of a patient. The mounting bracket may include an arcuate support frame having a plurality of mounts. The method may include coupling a first reference array to a first one of the plurality of mounts of the arcuate support frame. The method may also include determining a position of the bone of the patient based on a position of the reference array. Additionally, in some embodiments, the method may include supplying identification data related to the first one of the plurality of mounts. In such embodiments, the position of the bone of the patient may be determined based on the identification data.

The method may also include pivoting the arcuate support frame relative to the base. The method may further include generating angle data indicative of an angle between the base and the arcuate support frame. In such embodiments, the position of the bone of the patient may be determined based on the angle data. Additionally, the method may include moving the arcuate support frame relative to the base along an arcuate path defined by the arcuate support frame. The method may also include generating distance data indicative of the distance of the arcuate support frame along the arcuate path with respect to a predetermined position of the arcuate support frame. In such embodiments, the position of the bone of the patient may be determined based on the distance data. Yet further, the method may include decoupling the first reference array from the arcuate support frame and coupling the first reference array to a second one of the plurality of mounts of the arcuate support frame. The method may also include providing identification data of the second one of the plurality of mounts to a computer of the computer assisted orthopaedic surgery system. In such embodiments, the position of the bone of the patient may be determined based on the identification data. In some embodiments, the method may also include coupling a second reference array to a base of the mounting bracket. In such embodiments, the position of the bone of the patient may be determined based on the position of the first reference array relative to the second reference array.

According to a further aspect, a computer assisted orthopaedic surgery system may include a first reference array having a mounting end, a mounting bracket configured to be coupled to a bone of a patient, and a computer. The mounting bracket may include an arcuate support frame having a plurality of mounts. Each of the plurality of mounts may be configured to be coupled to the mounting end of the first reference array. The computer may be configured to determine the position of the bone of the patient based on a position of the first reference array. Additionally, in some embodiments, the computer may be configured to determine the position of the bone of the patient based on identification data related to at least one of the plurality of mounts.

The mounting bracket may include an angle sensor in some embodiments. The angle sensor may be configured to generate angle data indicative of an angle defined between the base and the arcuate support frame. In such embodiments, the computer may be configured to determine the position of the bone of the patient based on the angle data. Further, in some embodiments, the mounting bracket may include a distance sensor configured to generate distance data indicative of the distance of the arcuate support frame along an arcuate path defined by the arcuate support frame with respect to a predetermined position of the arcuate support frame. In such embodiments, the computer is configured to determine the position of the bone of the patient based on the distance data. The computer assisted orthopaedic surgery system may further include a second reference array. In such embodiments, the mounting bracket may include a base configured to be coupled to the bone of the patient and to the second reference array. Additionally, in such embodiments, the computer is configured to determine the position of the bone of the patient based on the position of the first reference array relative to second reference array.

BRIEF DESCRIPTION OF THE DRAWINGS

The detailed description particularly refers to the following figures, in which.

DETAILED DESCRIPTION OF THE DRAWINGS

Figure 1:
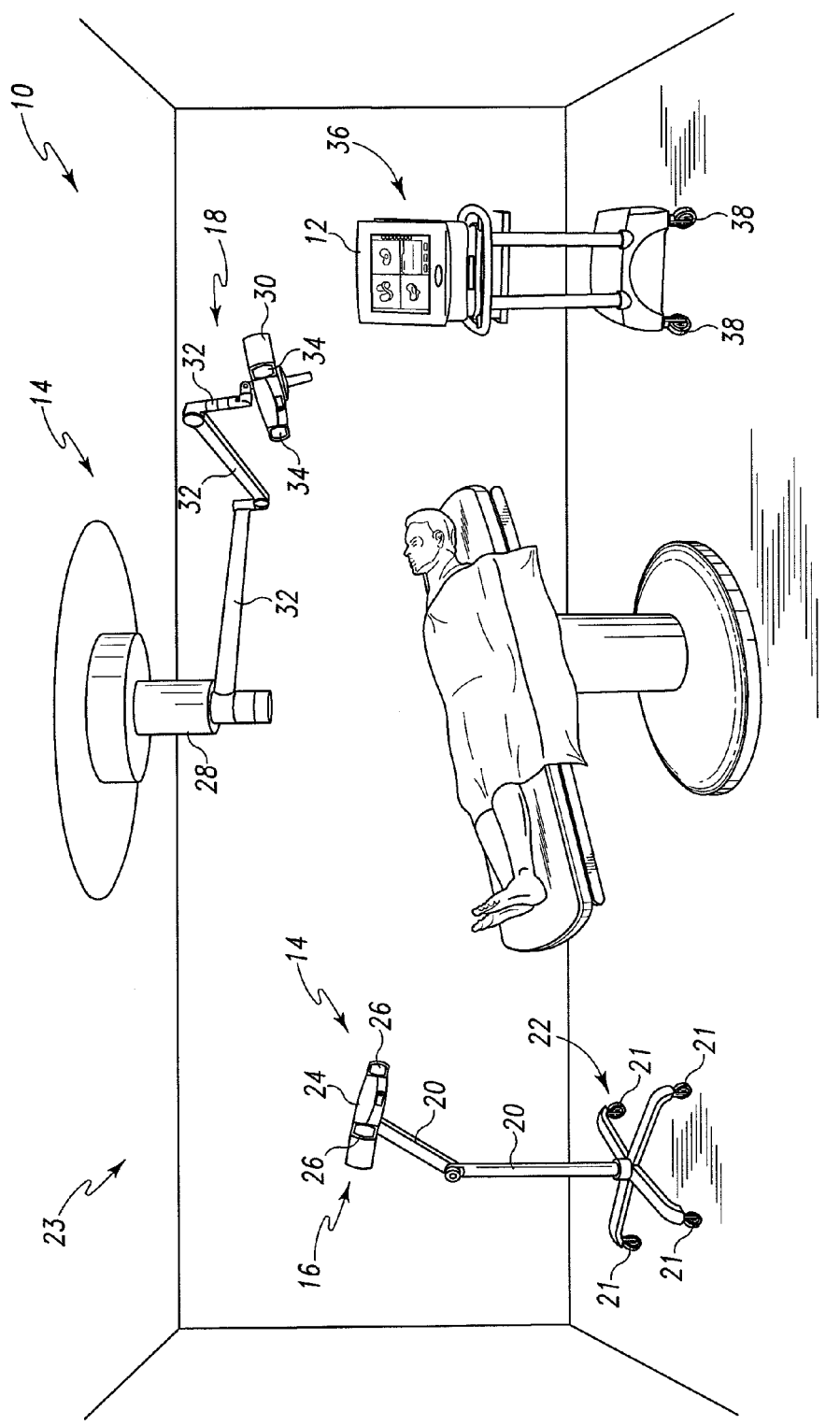
FIG. 1 is a perspective view of a computer assisted orthopaedic surgery (CAOS) system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a computer assisted orthopaedic surgery (CAOS) system 10 includes a computer 12 and a camera unit 14. The CAOS system 10 may be embodied as any type of computer assisted orthopaedic surgery system. Illustratively, the CAOS system 10 is embodied as one or more computer assisted orthopaedic surgery systems commercially available from DePuy Orthopaedics, Inc. of Warsaw, Ind.

and/or one or more computer assisted orthopaedic surgery systems commercially available from BrainLAB of Heimstetten, Germany. The camera unit 14 may be embodied as a mobile camera unit 16 or a fixed camera unit 18. In some embodiments, the system 10 may include both types of camera units 16, 18. The mobile camera unit 16 includes a stand 20 coupled with a base 22. The base 22 may include a number of wheels 21 to allow the mobile camera unit 16 to be repositioned within a hospital room 23. The mobile camera unit 16 includes a camera head 24. The camera head 24 includes two cameras 26. The camera head 24 may be positionable relative to the stand 20 such that the field of view of the cameras 26 may be adjusted. The fixed camera unit 18 is similar to the mobile camera unit 16 and includes a base 28, a camera head 30, and an arm 32 coupling the camera head 30 with the base 28. In some embodiments, other peripherals, such as display screens, lights, and the like, may also be coupled with the base 28. The camera head 30 includes two cameras 34. The fixed camera unit 18 may be coupled to a ceiling, as illustratively shown in FIG. 1, or a wall of the hospital room. Similar to the camera head 24 of the camera unit 16, the camera head 30 may be positionable relative to the arm 32 such that the field of view of the cameras 34 may be adjusted. The camera units 14, 16, 18 are communicatively coupled with the computer 12. The computer 12 may be mounted on or otherwise coupled with a cart 36 having a number of wheels 38 to allow the computer 12 to be positioned near the surgeon during the performance of the orthopaedic surgical procedure.

Figure 2:
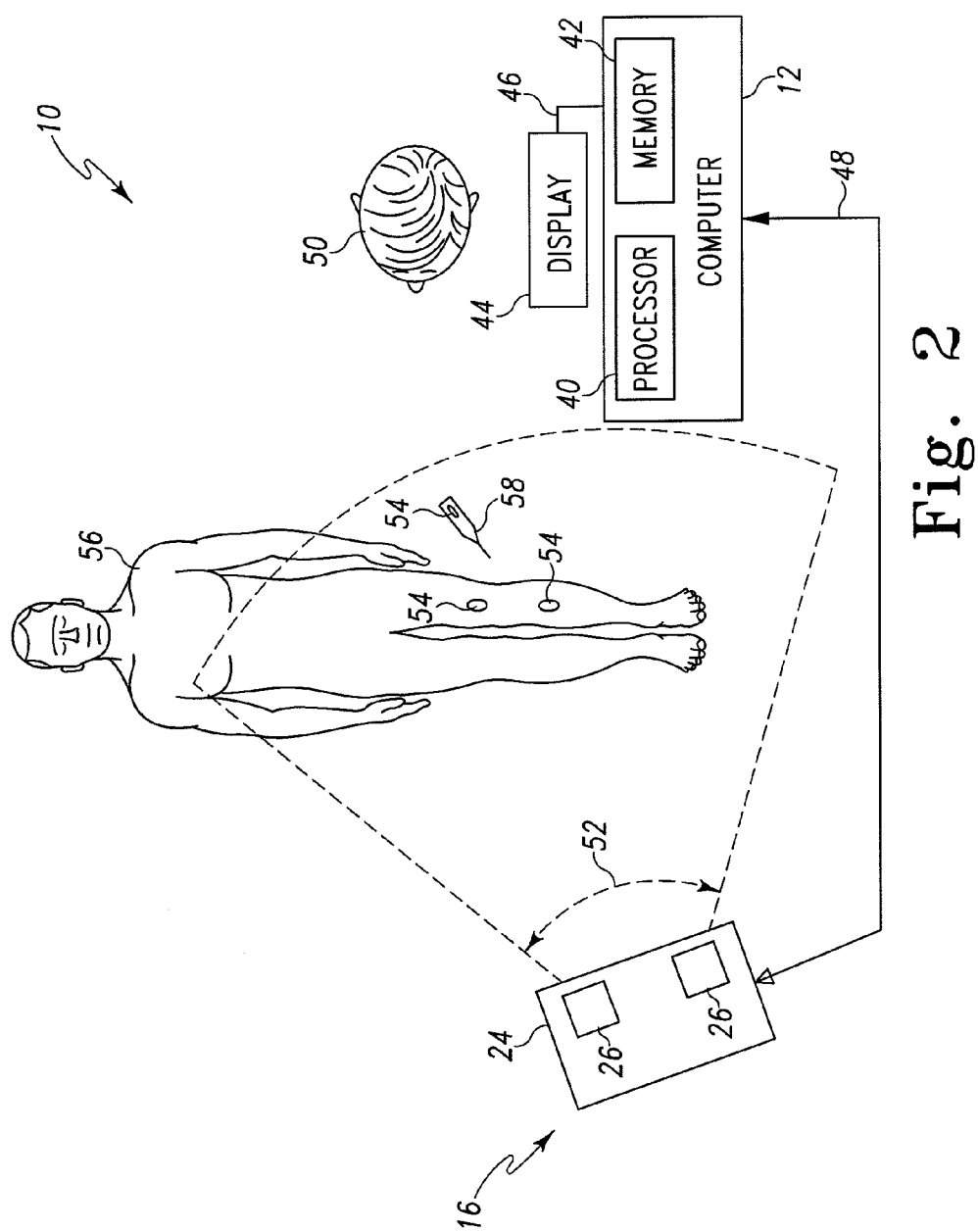
FIG. 2 is a simplified diagram of the CAOS system of FIG. 1.

Referring now to FIG. 2, the computer 12 illustratively includes a processor 40 and a memory device 42. The processor 40 may be embodied as any type of processor including, for example, discrete processing circuitry (e.g., a collection of logic devices), general purpose integrated circuit(s), and/or application specific integrated circuit(s) (i.e., ASICs). The memory device 42 may be embodied as any type of memory device and may include one or more memory types, such as, random access memory (i.e., RAM) and/or read-only memory (i.e., ROM). In addition, the computer 12 may include other devices and circuitry typically found in a computer for performing the functions described herein such as, for example, a hard drive, input/output circuitry, and the like.

The computer 12 is communicatively coupled with a display device 44 via a communication link 46. Although illustrated in FIG. 2 as separate from the computer 12, the display device 44 may form a portion of the computer 12 in some embodiments. Additionally, in some embodiments, the display device 44 or an additional display device may be positioned away from the computer 12. For example, the display device 44 may be coupled with the ceiling or wall of the operating room wherein the orthopaedic surgical procedure is to be performed. Additionally or alternatively, the display device 44 may be embodied as a virtual display such as a holographic display, a body mounted display such as a heads-up display, or the like. The computer 12 may also be coupled with a number of input devices such as a keyboard and/or a mouse for providing data input to the computer 12. However, in the illustrative embodiment, the display device 44 is a touch-screen display device capable of receiving inputs from an orthopaedic surgeon 50. That is, the surgeon 50 can provide input data to the computer 12, such as making a selection from a number of on-screen choices, by simply touching the screen of the display device 44.

The computer 12 is also communicatively coupled with the camera unit 16 (and/or 18) via a communication link 48. Illustratively, the communication link 48 is a wired communication link but, in some embodiments, may be embodied as a wireless communication link. In embodiments wherein the communication link 48 is a wireless signal path, the camera unit 16 and the computer 12 include wireless transceivers such that the computer 12 and camera unit 16 can transmit and receive data (e.g., image data). Although only the mobile camera unit 16 is shown in FIG. 2, it should be appreciated that the fixed camera unit 18 may alternatively be used or may be used in addition to the mobile camera unit 16.

Figure 3:
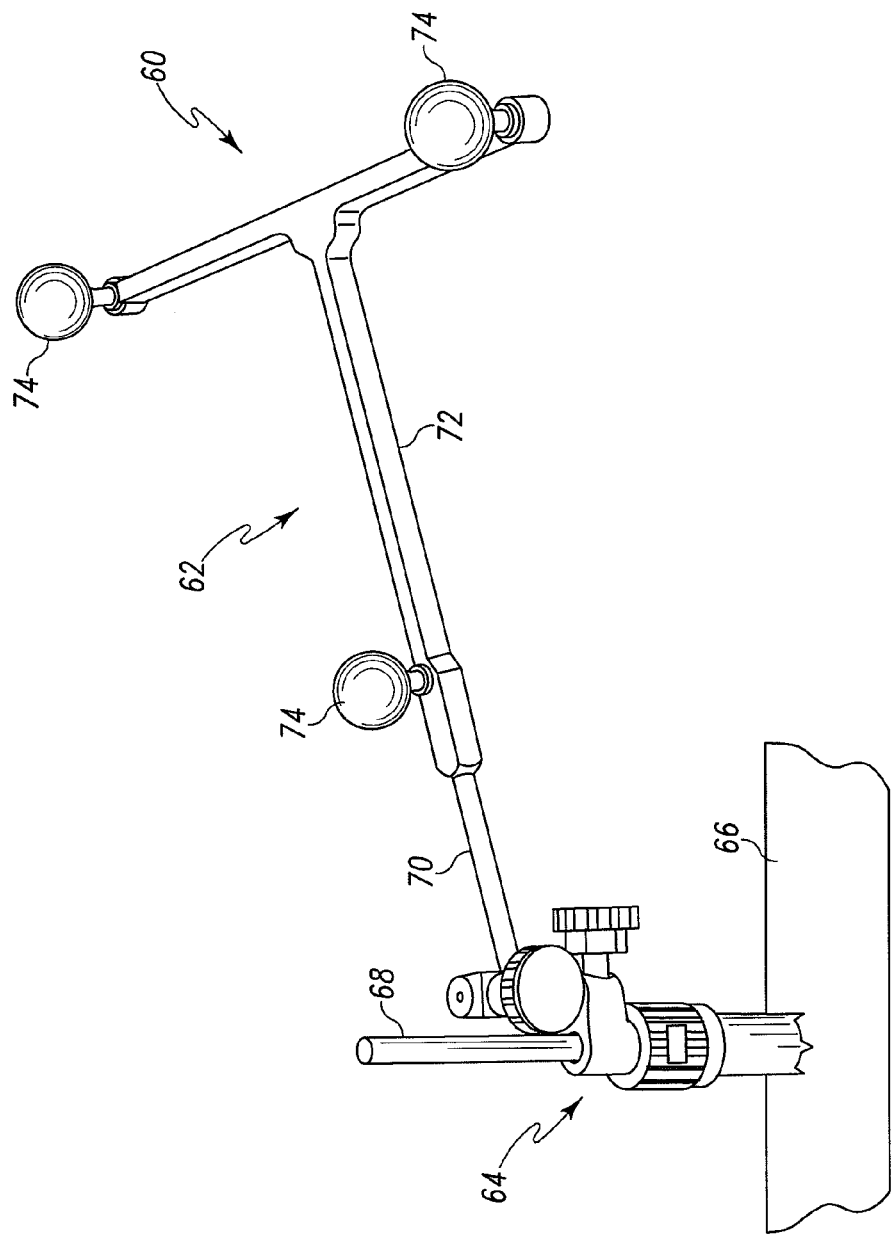
FIG. 3 is a perspective view of a bone locator tool.

The CAOS system 10 may also include a number of reference arrays 54, which may be coupled the relevant bones of a patient 56 and/or with orthopaedic surgical tools 58. For example, as illustrated in FIG. 3, a tibial array 60 includes a reference array 62 and bone clamp 64. The illustrative bone clamp 64 is configured to be coupled with a tibia bone 66 of the patient 56 using a Schantz pin 68, but other types of bone clamps may be used. The reference array 62 is coupled with the bone clamp 64 via an extension arm 70. The reference array 62 includes a frame 72 and three reflective elements or sensors 74. The reflective elements 74 are embodied as spheres in the illustrative embodiment, but may have other geometric shapes in other embodiments. Additionally, in other embodiments reference arrays having more than three reflective elements may be used. The reflective elements 74 are positioned in a predefined configuration that allows the computer 12 to determine the identity of the tibial array 60 based on the configuration. That is, when the tibial array 60 is positioned in a field of view 52 of the camera head 24, as shown in FIG. 2, the computer 12 is configured to determine the identity of the tibial array 60 based on the images received from the camera head 24. Additionally, based on the relative position of the reflective elements 74, the computer 12 is configured to determine the location and orientation of the tibial array 60 and, accordingly, the tibia 66 to which the array 60 is coupled.

Figure 4:
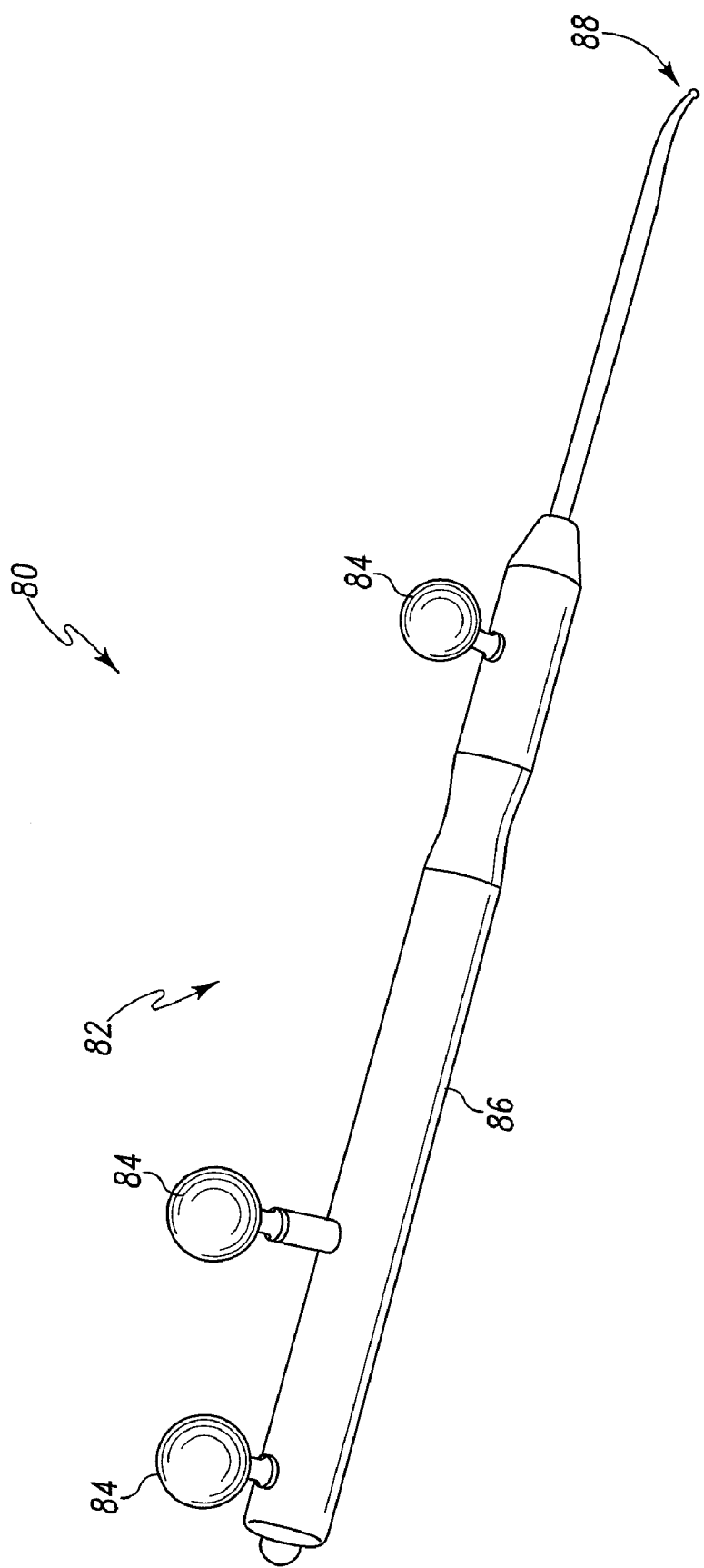
FIG. 4 is a perspective view of a registration tool for use with the system of FIG. 1.
Figure 5:
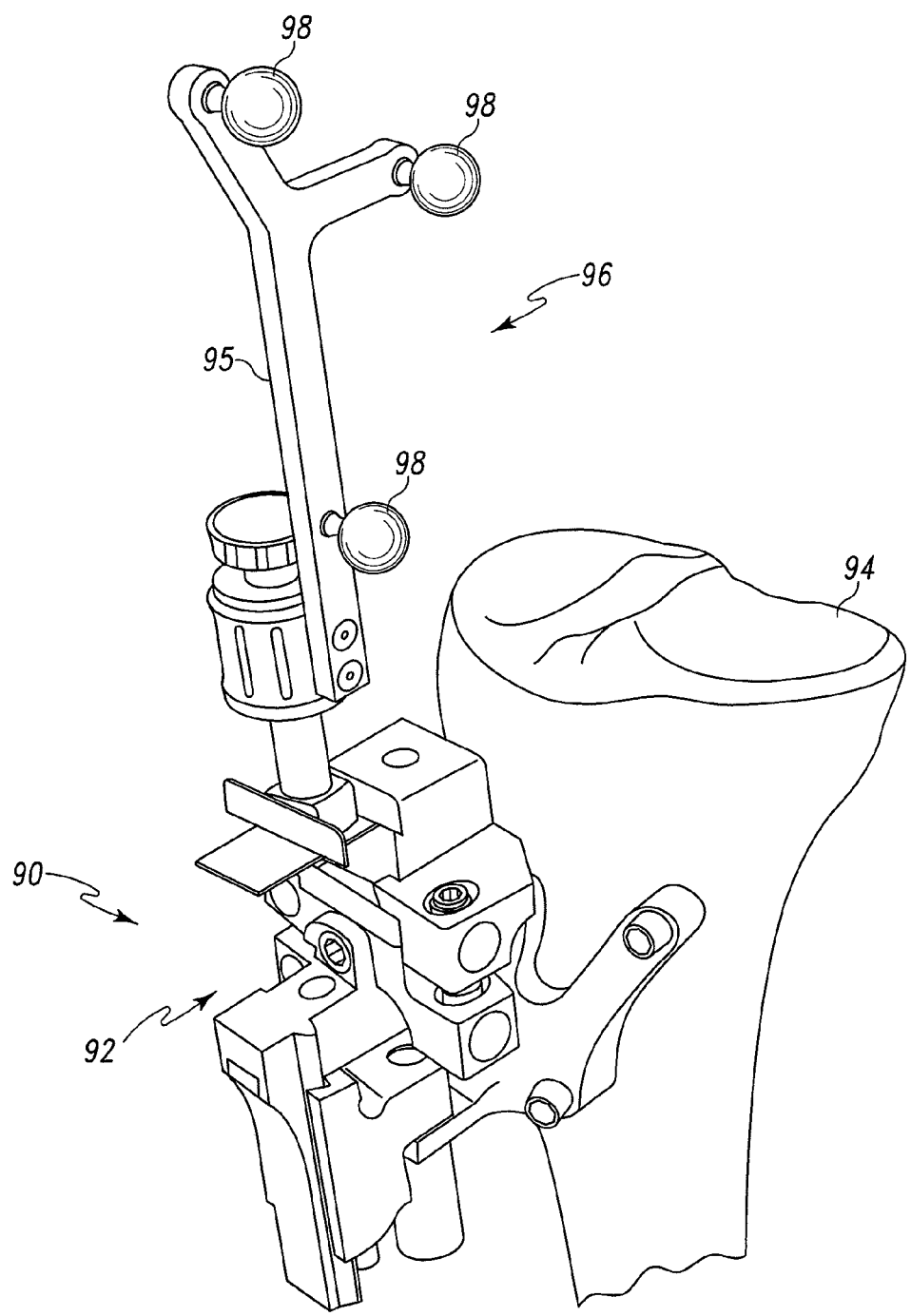
FIG. 5 is a perspective view of an orthopaedic surgical tool for use with the system of FIG. 1.

Reference arrays may also be coupled to other surgical tools. For example, a registration tool 80, as shown in FIG. 4, is used to register points of a bone of the patient. The registration tool 80 includes a reference array 82 having three reflective elements 84 coupled with a handle 86 of the tool 80. The registration tool 80 also includes pointer end 88 that is used to register points of a bone. The reflective elements 84 are also positioned in a configuration that allows the computer 12 to determine the identity of the registration tool 80 and its relative location (i.e., the location of the pointer end 88). Additionally, reference arrays may be used on other surgical tools such as a tibial resection jig 90, as illustrated in FIG. 5. The jig 90 includes a resection guide portion 92 that is coupled with a tibia bone 94 at a location of the bone 94 that is to be resected. The jig 90 includes a reference array 96 that is coupled with the portion 92 via a frame 95. The reference array 96 includes three reflective elements 98 that are positioned in a configuration that allows the computer 12 to determine the identity of the jig 90 and its relative location (e.g., with respect to the tibia bone 94).

The CAOS system 10 may be used by the orthopaedic surgeon 50 to assist in any type of orthopaedic surgical procedure including, for example, a total knee replacement procedure. To do so, the computer 12 and/or the display device 44 are positioned within the view of the surgeon 50. As discussed above, the computer 12 may be coupled with a movable cart 36 to facilitate such positioning. The camera unit 16 (and/or camera unit 18) is positioned such that the field of view 52 of the camera head 24 covers the portion of a patient 56 upon which the orthopaedic surgical procedure is to be performed, as shown in FIG. 2.

During the performance of the orthopaedic surgical procedure, the computer 12 of the CAOS system 10 is programmed or otherwise configured to display images of the individual surgical procedure steps that form the orthopaedic surgical procedure being performed. The images may be graphically rendered images or graphically enhanced photographic images. For example, the images may include three-dimensional rendered images of the relevant anatomical portions of a patient. The surgeon 50 may interact with the computer 12 to display the images of the various surgical steps in sequential order. In addition, the surgeon may interact with the computer 12 to view previously displayed images of surgical steps, selectively view images, instruct the computer 12 to render the anatomical result of a proposed surgical step or procedure, or perform other surgical related functions. For example, the surgeon may view rendered images of the resulting bone structure of different bone resection procedures. In this way, the CAOS system 10 provides a surgical "walkthrough" for the surgeon 50 to follow while performing the orthopaedic surgical procedure.

In some embodiments, the surgeon 50 may also interact with the computer 12 to control various devices of the system 10. For example, the surgeon 50 may interact with the system 10 to control user preferences or settings of the display device 44. Further, the computer 12 may prompt the surgeon 50 for responses. For example, the computer 12 may prompt the surgeon to inquire if the surgeon has completed the current surgical step, if the surgeon would like to view other images, and the like.

The camera unit 16 and the computer 12 also cooperate to provide the surgeon with navigational data during the orthopaedic surgical procedure. That is, the computer 12 determines and displays the location of the relevant bones and the surgical tools 58 based on the data (e.g., images) received from the camera head 24 via the communication link 48. To do so, the computer 12 compares the image data received from each of the cameras 26 and determines the location and orientation of the bones and tools 58 based on the relative location and orientation of the reference arrays 54, 62, 82, 96. The navigational data displayed to the surgeon 50 is continually updated. In this way, the CAOS system 10 provides visual feedback of the locations of relevant bones and surgical tools for the surgeon 50 to monitor while performing the orthopaedic surgical procedure.

Figure 6:
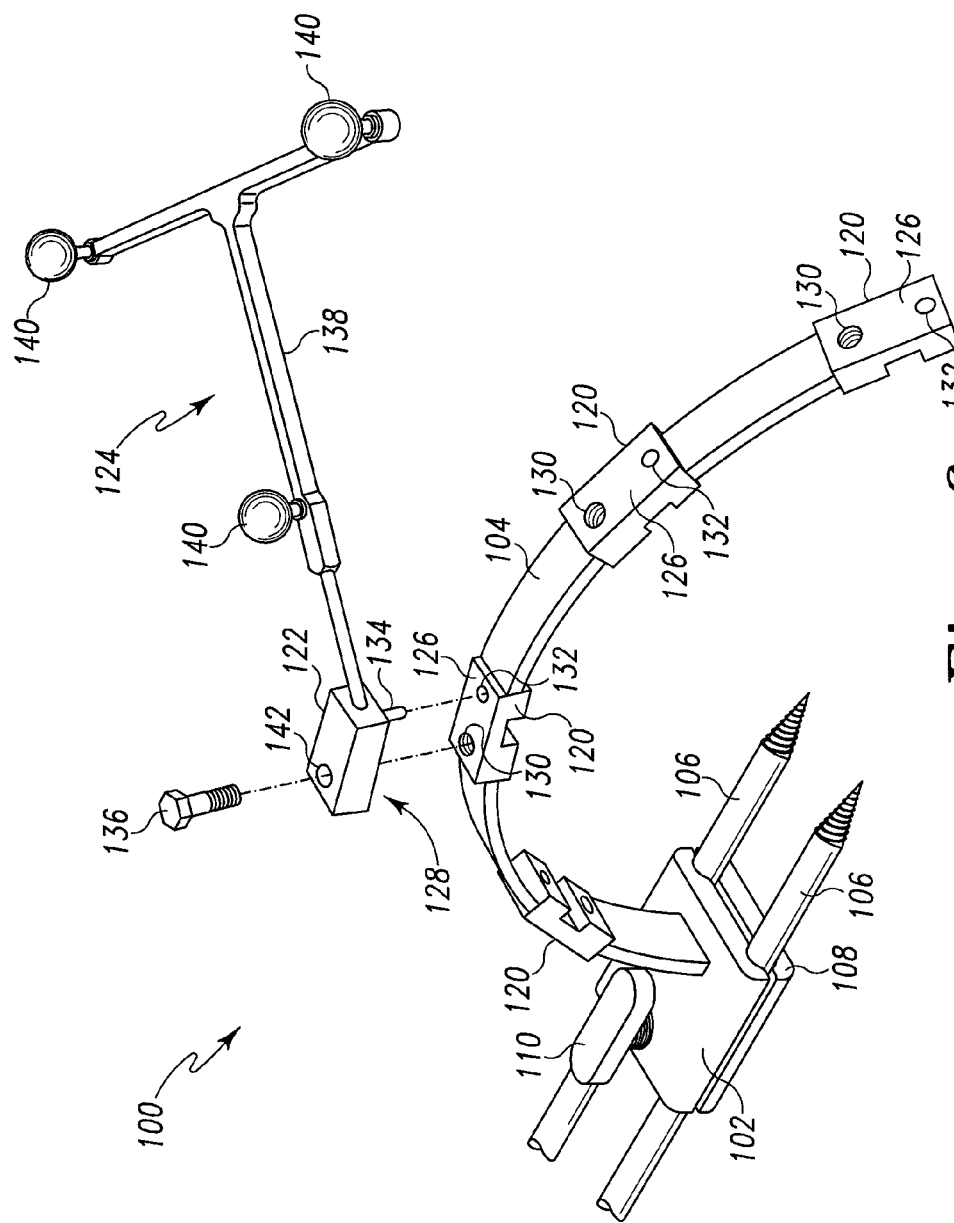
FIG. 6 is perspective view of a mounting bracket for use with a reference array of the computer assisted orthopaedic surgery system of FIG. 1.
Figure 7:
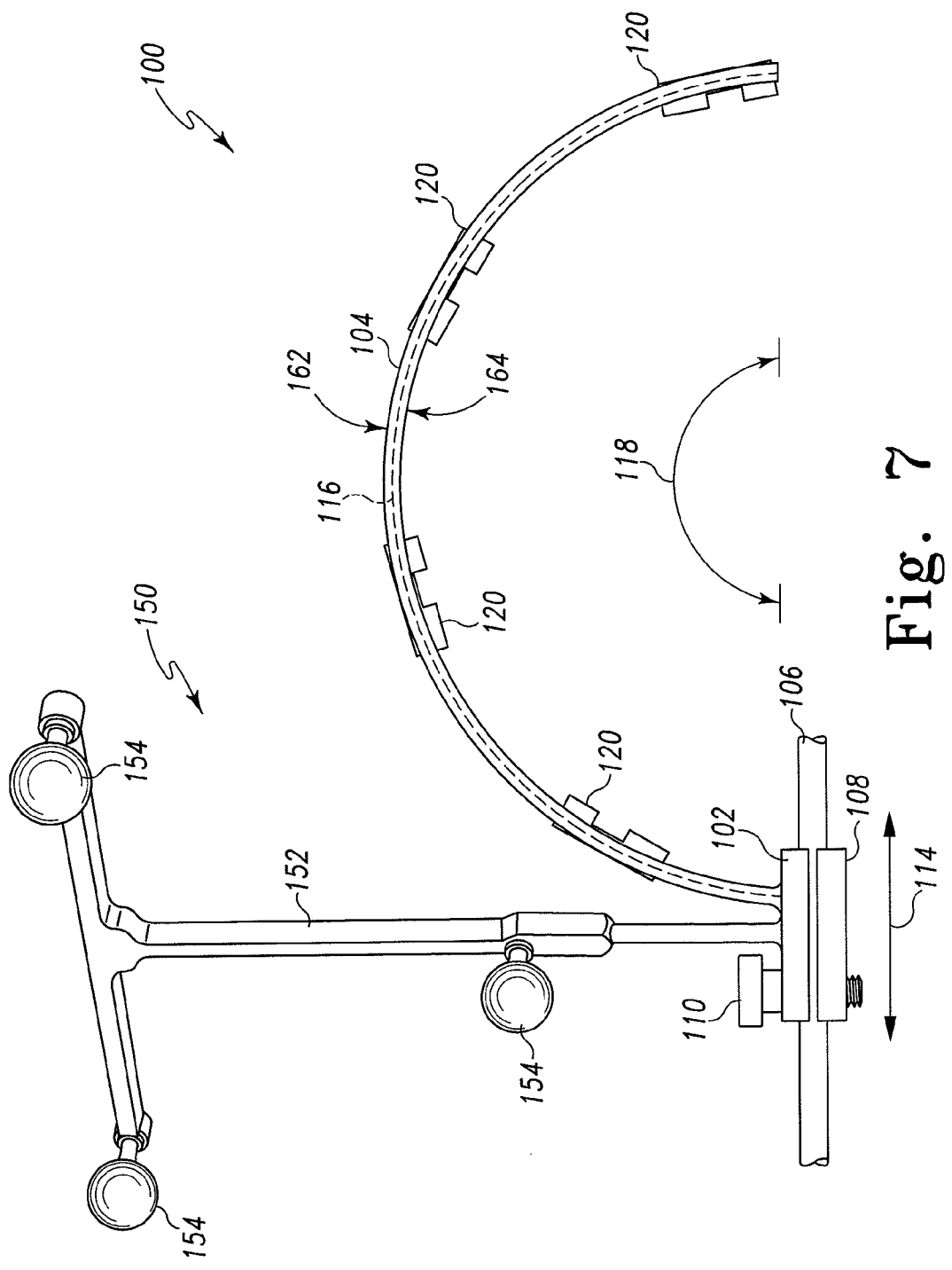
FIG. 7 is a side elevation view of the mounting bracket of FIG. 6.
Figure 9:
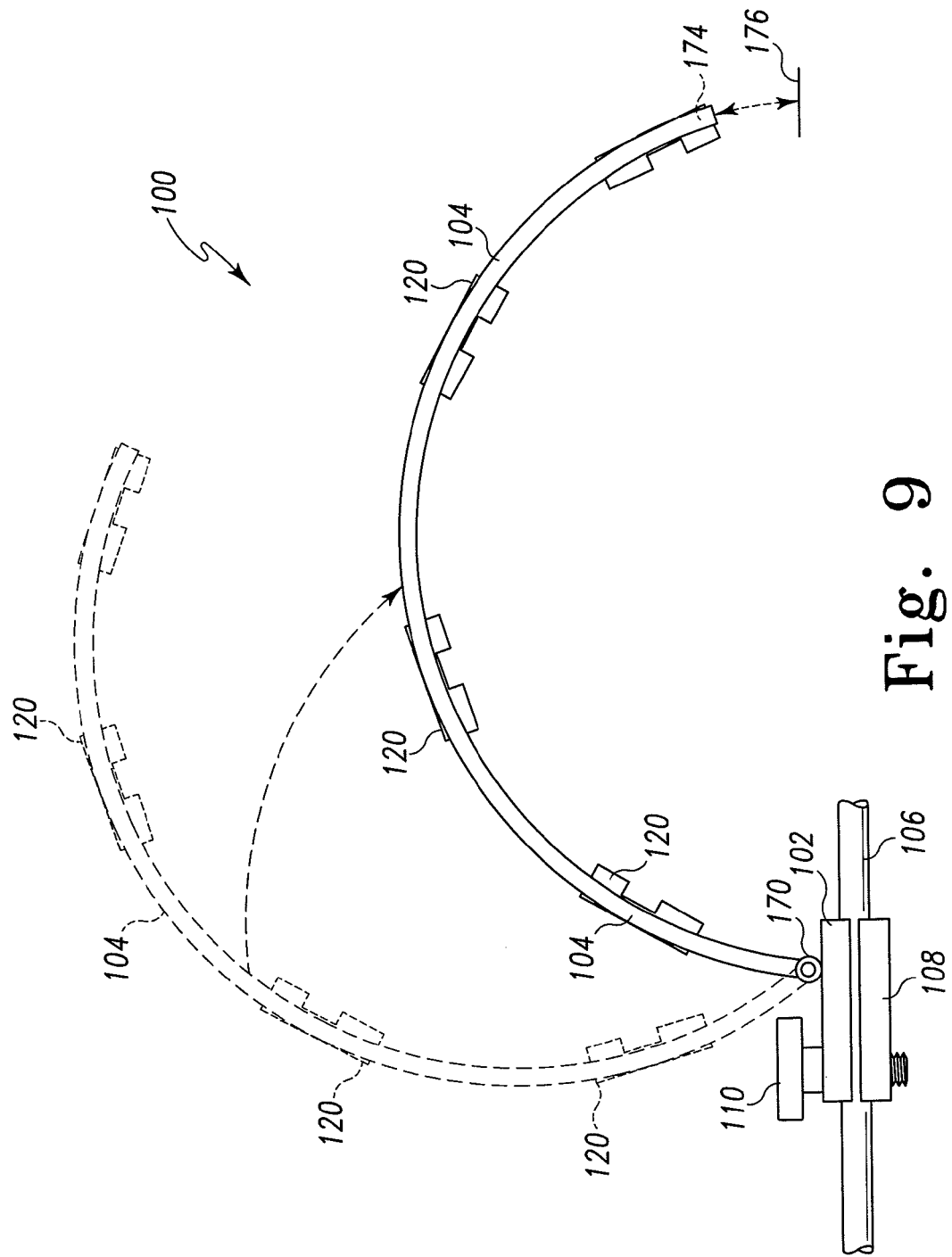
FIG. 9 is a side elevation view of the mounting bracket of FIG. 6.
Figure 11:
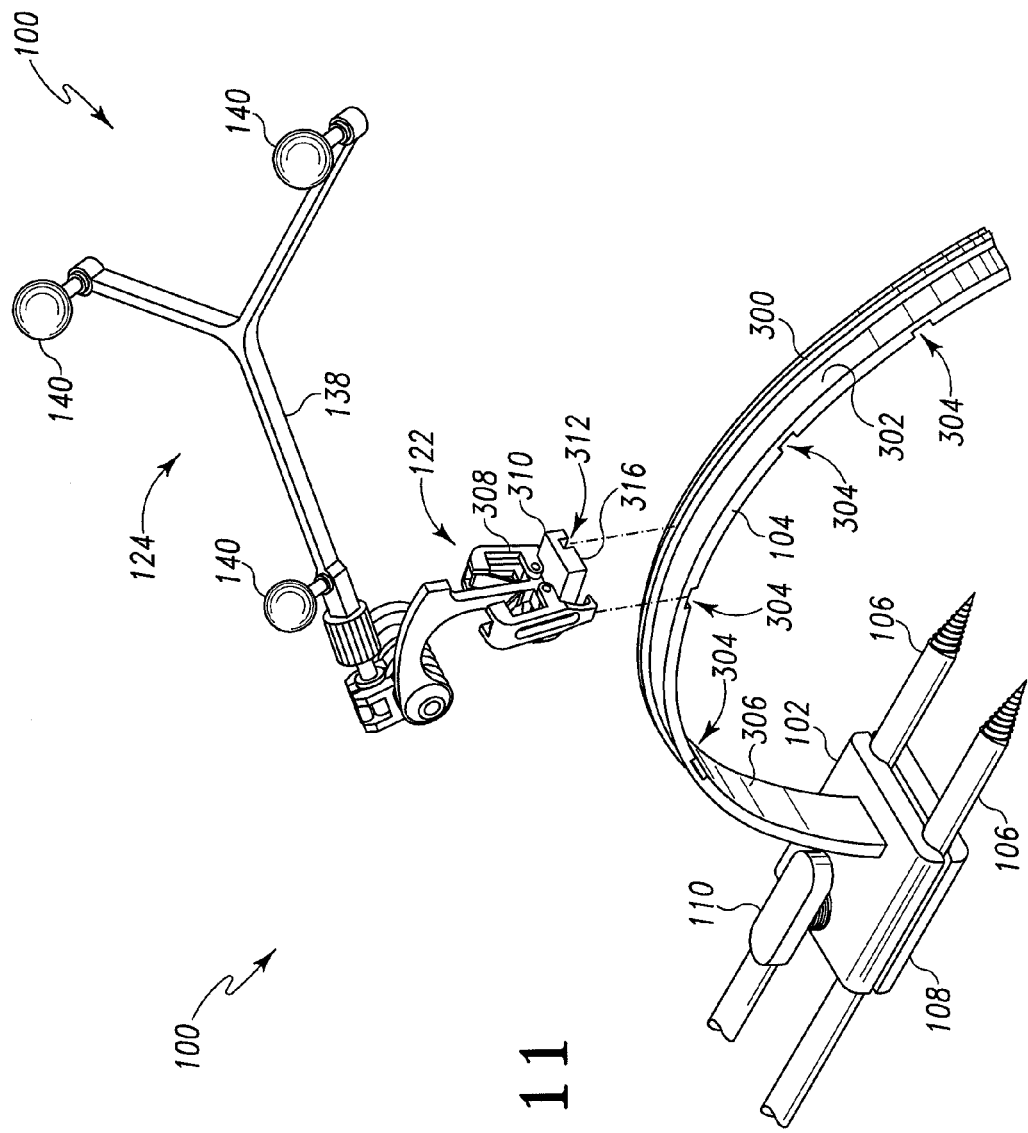
FIG. 11 is a perspective view of a further embodiment of the mounting bracket of FIG. 6.

Referring now to FIGS. 6 and 7, in another embodiment, a mounting bracket 100 includes a base 102 and an arcuate support frame 104. The arcuate support frame 104 is coupled to the base 102 and, in some embodiments as described below in regard to FIGS. 9 and 11, is movable with respect to the base 102. The base 102 is configured to be coupled to a bone, such as the scapula or the humerus, of the patient 56. In the illustrative embodiment of FIG. 6, the base 102 is configured to be coupled to the bone of the patient 56 via use of two bone screws 106. However, in other embodiments, other types of securing devices may be used to couple the base 102 to the bone of the patient 56 such as, for example, bone pins, bone nails, or the like.

In the illustrative embodiment, the base 102 includes a bottom clamp 108 and a thumbscrew 110. The base 102 and bottom clamp 108 define two apertures 112 (see FIG. 9) through which the bone screws 106 extend. The thumbscrew 110 may be adjusted to move the bottom clamp 108 toward or away from the base 102. When the thumbscrew 110 is tightened, the bottom clamp 108 moves toward the base 102 and decreases the overall size of the apertures 112 such that the base 102 and bottom clamp 108 are secured to the bone screws 106 in a fixed position. The base 102 may be repositioned by loosening the thumbscrew 110, moving the base 102 along the length of the bone screws 106 in a linear direction 114 as illustrated in FIG. 7, and retightening the thumbscrew 110 to secure the base 102 and bottom clamp 108 to the bone screws 106 in the new location. Because the base 102 may be secured to the bone screws 106 at any point along the length of the screws 106, the mounting bracket 100 is usable with patients having various body configurations such as various thicknesses of soft tissue over the relevant bone(s).

The arcuate support frame 104 extends from the base 102 about a predefined arc. In the embodiment illustrated in FIG. 7, the arcuate support frame 104 has an arc length 116 subtending an angle 118 of about 180 degrees. However, in other embodiments, the arcuate support frame 104 may be any length subtending an angle of any size depending on the intended application for the mounting bracket 100. For example, in one particular embodiment, a mounting bracket 100 configured to be coupled to the humerus of the patient has an arcuate support frame 104 that subtends an angle of about 120 degrees and a separate mounting bracket 100 configured to be coupled to the scapula of the patient has an arcuate support frame 104 that subtends an angle of about 150 degrees.

It should be appreciated that although the arcuate support frame 104 is shown as a substantially continuous curve, a similar arcuate shape may be achieved by use of a series of segments positioned adjacent one another to form a generally curved shape. Moreover, in other embodiments, the mounting bracket 100 may include a support frame having other generally curved geometric shapes such an open square, octagon, pentagon, or other open geometric shape.

The arcuate support frame 104 includes a number of mounts 120 configured to receive a mounting end 122 of a reference array 124. In the illustrative embodiment, the mounts 120 are evenly positioned along the length of the arcuate support frame 104. However, in other embodiments, the mounts 120 may be positioned in any configuration along the length of the arcuate support frame 104. In the illustrative embodiment of FIGS. 6 and 7, each of the mounts 120 includes a top planar surface 126 configured to abut or confront a bottom planar surface 128 of the mounting end 122 of the reference array 124 when the reference array 124 is coupled to the arcuate support frame 104. However, in other embodiments, the mounts 120 may include a top surface having any shape couplable with a bottom surface of the mounting end 122 of the reference array 124. For example, in some embodiments, the top surface of the mounts 120 and the bottom surface of the mounting end 122 of the reference array 122 may be curved.

In the illustrative embodiment, each of the mounts 120 includes a threaded aperture 130 and a guide pin-receiving aperture 132 to facilitate attachment of the reference array 120 to the arcuate support frame 104. The guide pin-receiving aperture 132 is positioned on the planar surface 122 and sized to receive a guide pin 134 of the mounting end 122 of the reference array 124. The threaded aperture 130 is configured to receive a portion of a screw 136, or other securing device, to secure the reference array 124 to the arcuate support frame 104. As such, the reference array 124 may be secured to any mounting positions 120 of the arcuate support frame 104 by coupling the mounting end 122 of the reference array to the desired mount 120 such that the guide pin 134 of the mounting end 122 is received by the guide pin-receiving aperture 132. The reference array 124 may be secured in position to the arcuate support frame 104 by inserting the screw 136 through a guide aperture 142 of the mounting end 118 and screwing the screw 136 into the threaded aperture 130. At any point during the orthopaedic surgical procedure, as discussed in more detail below in regard to algorithm 200 illustrated in FIG. 13, the reference array 124 may be decoupled from the arcuate support frame 104 and secured to a new mount 120 of the frame 104.

Although the arcuate support frame 104 illustrated in FIGS. 6 and 7 include mounts 120 having a threaded and guide pin-receiving apertures, 130, 132, respectively, the mounts 120 may include other coupling mechanisms in other embodiments. For example, in some embodiments, the mounts may include two or more guide pin receiving apertures having different diameters. In such embodiments, the mounting end 122 of the reference array 124 includes a corresponding number of guide pins having different diameters such that the mounting end 122 is coupleable to the mounts 120 in a single orientation. Additionally, in such embodiments, the mounting end 122 may include a clamp or similar device for securing the reference array 124 to the arcuate support frame 104. Yet further, in other embodiments, the reference array 124 may be coupleable to the arcuate support frames 104 using other mechanisms and/or methodologies such as those described below in regard to FIGS. 11-13.

The arcuate support frame 104 may be formed from any material capable of supporting the reference array 124 without significantly deforming due to the weight of the reference array 124. In one particular embodiment, the reference array is formed from a carbon fiber material, but in other embodiments, other types of materials such as steel or plastic may be used. In some embodiments, the arcuate support frame 104 and the base 102 are integral to each other. In such embodiments, the base 102 is formed from the same material as the support frame 104. Additionally, in some embodiments, the mounting bracket 100 may be provided to the surgeon 50 in a sterile state. For example, the mounting bracket 100 may be stored in a sterilized package. In such embodiments, the mounting bracket 100 may be sterilized prior to or subsequent to being packaged. Additionally, in embodiments wherein the mounting bracket 100 is reused, the bracket 100 may be re-sterilized after each orthopaedic surgical procedure via any suitable method such as, for example, via use of an autoclave.

The reference array 124 is substantially similar to the reference arrays 54, 62, 82, 96. The reference array 124 includes a frame 138 coupled to the mounting end 122 and three reflective elements or sensor 140. Similar to the reference arrays 54, 62, 82, 96, the illustrative reflective elements 140 are embodied as spheres, but may have other geometric shapes in other embodiments. Additionally, in other embodiments, the reference array 124 may have more than three reflective elements may be used. The reflective elements 140 are positioned in a predefined configuration that allows the computer 12 to determine the identity of the reference array 124 and/or mounting bracket 100 based on the configuration. For example, when the reference array 124 is positioned in the field of view 52 of the camera head 24, the computer 12 is configured to determine the identity of the reference array 124 and mounting bracket 100 based on the images received from the camera head 24.

In some embodiments, a reference array 150 is also coupled to the base 102 of the mounting bracket 100 as illustrated in FIG. 7. The reference array 150 may be integral to the base 102 or may be removable therefrom. The reference array 150 is substantially similar to the reference array 124 and includes a frame 152 and three reflective elements or sensor 154. The illustrative reflective elements 154 are embodied as spheres, but may have other geometric shapes in other embodiments. Additionally, in other embodiments the reference array 150 may have more than three reflective elements. As with the reference array 124, the reflective elements 154 of the reference array 150 are positioned in a predefined configuration that allows the computer 12 to determine the identity of the reference array 150 and/or mounting bracket 100 based on the configuration. The frame 152 of the reference array 150 is coupled to the base 102 via an extension rod 156. The extension rod 156 may have any length depending on the particular embodiment. In one embodiment, the extension rod 156 is adjustable such that the reference array 150 may be moved closer or farther away from the base 102.

Figure 8:
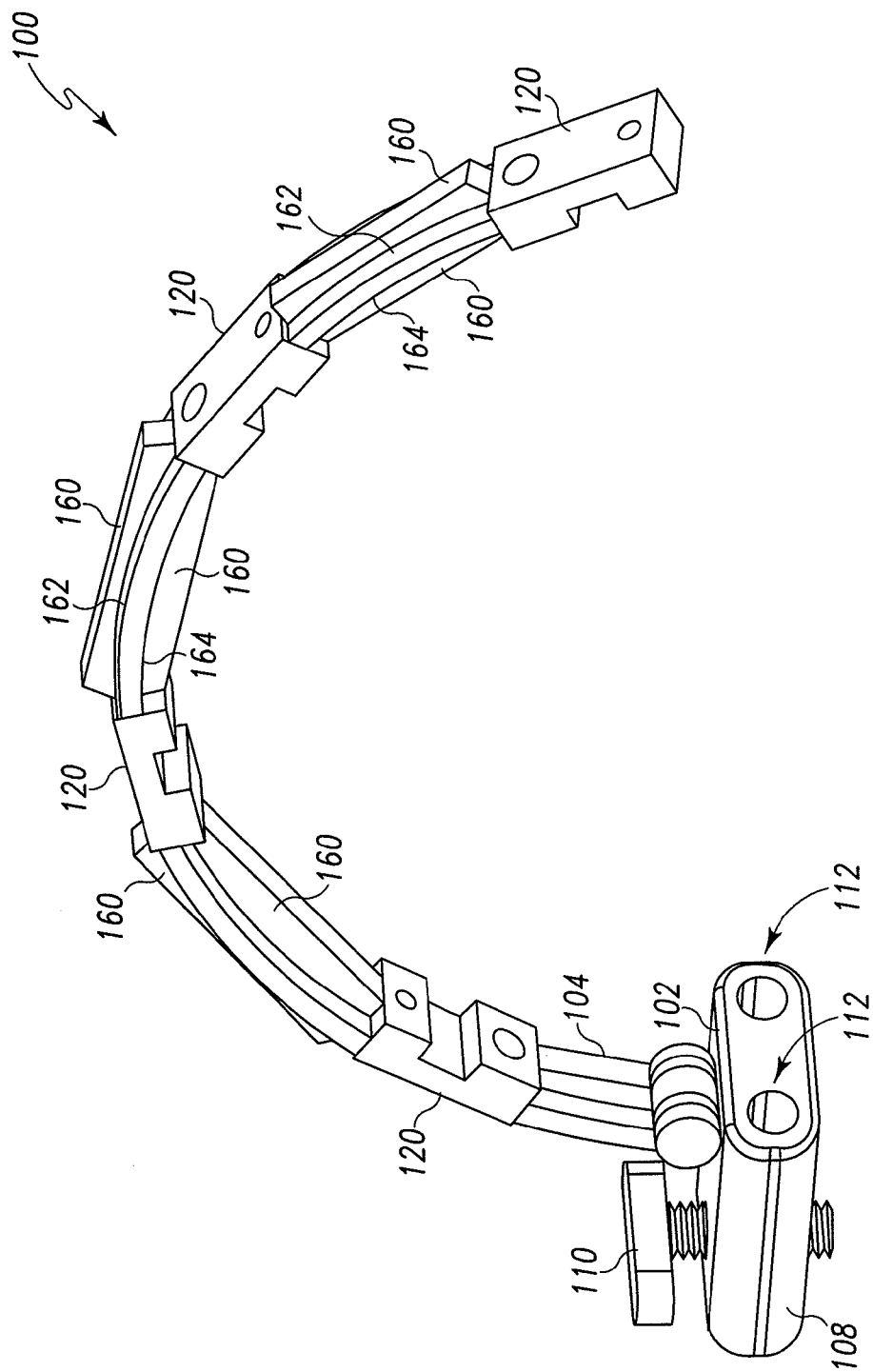
FIG. 8 is a perspective view of another embodiment of the mounting bracket of FIG. 6.

Referring now to FIG. 8, in some embodiments, the mounting bracket 100 may include a number of rib supports 160 on the arcuate support frame 104. The rib supports 160 are located between each of the mounts 120. The rib supports 160 may be positioned between the mounts 120 on an outer curved surface 162 and/or on an inner curved surface 164 of the arcuate reference array 104. The rib supports 160 may form an integral part of the reference array 104 or may be separate therefrom but coupled to the outer curved surface 162 and/or the inner curved surface 164. The rib supports 160 provide an additional amount of support to the arcuate support frame 104 so as to reduce the likelihood that the arcuate support frame 104 deforms when the reference array 124 is coupled thereto. As illustrated in FIG. 8, the rib supports 160 have a substantially rectangular side profile, but may have any configuration in other embodiments that provides additional support to the arcuate support frame 104. Additionally, in some embodiments, the arcuate support frame 104 may have a circular or oval cross-section to increase the stiffness of the frame 104 and, thereby, further reduce the likelihood that the arcuate support frame 104 deforms when the reference array 124 is coupled thereto.

Referring now to FIG. 9, in some embodiments, the arcuate support frame 104 may be coupled to the base 102 via a hinge 170 such that reference array is pivotable with respect to the base 102. In such embodiments, the hinge 170 or other portion of the bracket 100 may include a locking mechanism (not shown) such that the arcuate support frame 104 may be secured in position after being pivoted. Once the hinge 170 is locked in this manner, the arcuate support frame 104 is non-pivotable with respect to the base 102. In this way, the arcuate support frame 104 may be pivoted to a desired position, locked in the desired position, and the reference array 124 may then be coupled to the arcuate support frame 104 without causing the arcuate support frame 104 to pivot from the desired position.

Figure 10:
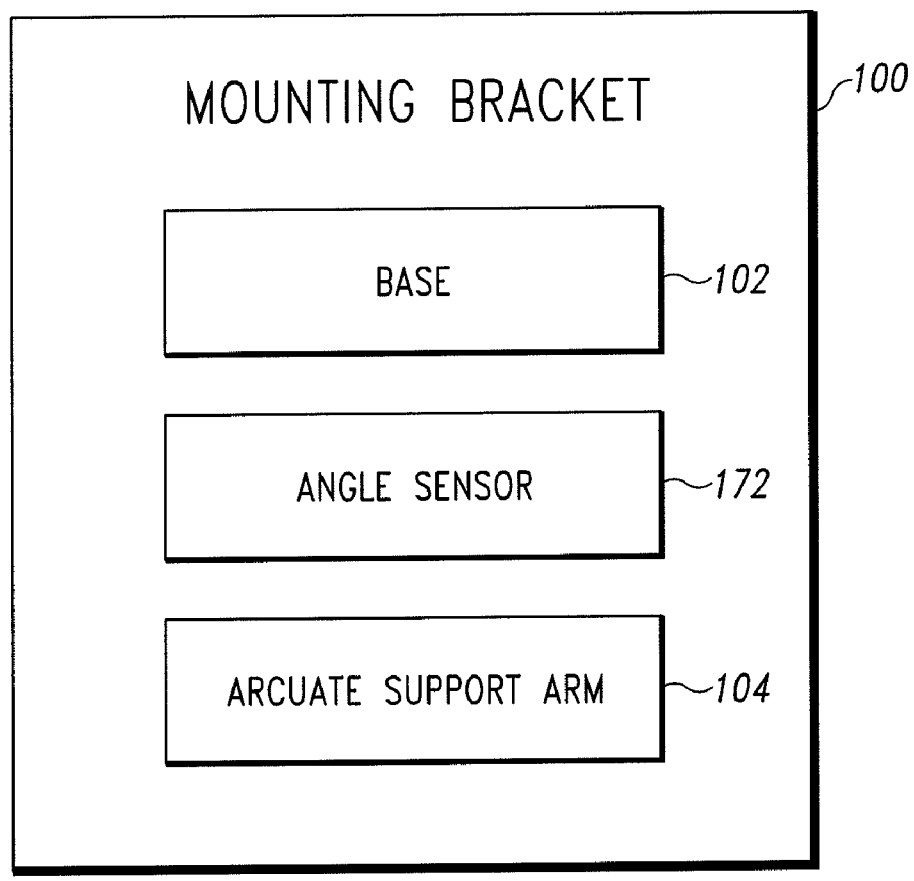
FIG. 10 is a block diagram of the mounting bracket of FIG. 9.

In the embodiment illustrated in FIG. 9, the mounting bracket 100 also includes an angle sensor 172 as illustrated in FIG. 10. The angle sensor 172 is configured to generate a data signal indicative of the angle between the arcuate support frame 104 and a predetermined reference point or plane. For example, in one embodiment, the angle sensor 172 is configured to generate data indicative of an angle 174 (see FIG. 9) defined between the arcuate support frame 104 and a plane 176 defined by the base 102. In such embodiments, the angle data generated by the angle sensor 172 is transmitted to the computer 12. To do so, the angle sensor 172 may be communicatively coupled to the computer 12 via a number of communication links such as wires, cables, or the like. Alternatively, the mounting bracket 100 may include a transmitter configured to transmit the angle data from the angle sensor 172 to the computer 12. As discussed in more detail below in regard to FIG. 16, the computer 12 is configured to use the angle data in the determination of the position of the reference array 124, and thereby the bone of the patient 56 to which the mounting bracket 100 is coupled.

Figure 12:
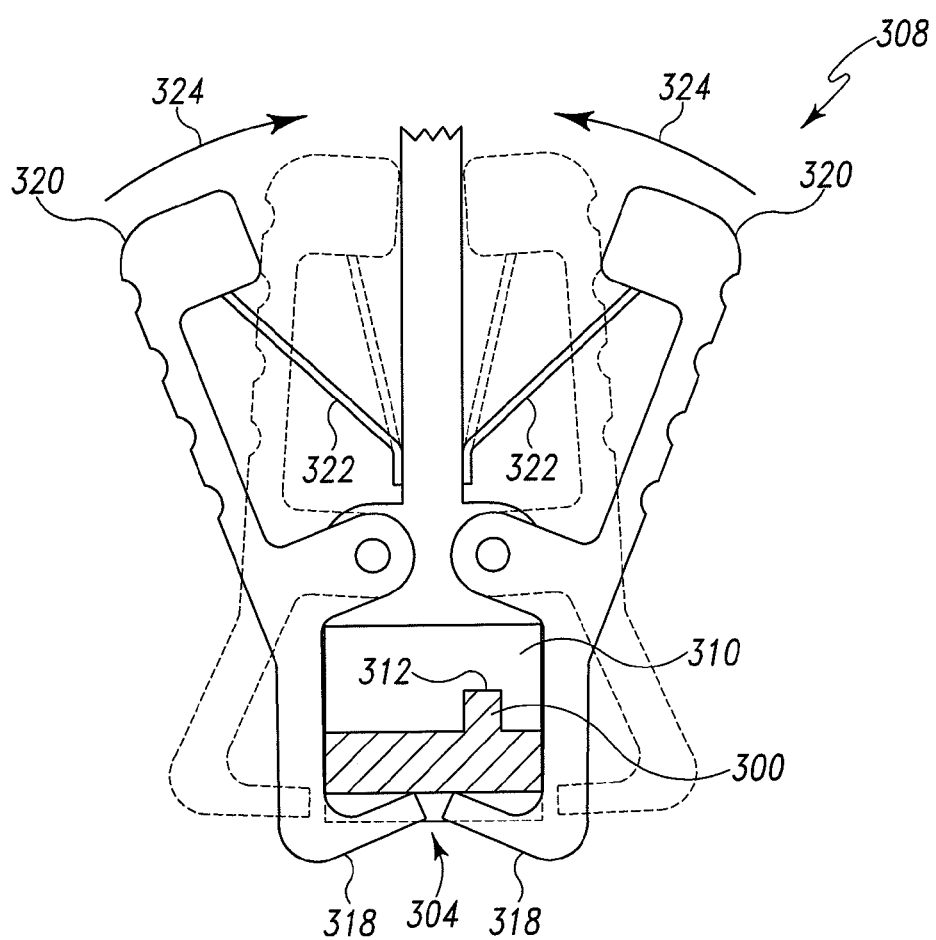
FIG. 12 is a cross-sectional view of the mounting bracket of FIG. 11 having a reference array coupled thereto.

Referring now to FIGS. 11 and 12, in another embodiment, the arcuate support frame 104 includes a rail 300 defined on a top surface 302. The rail 300 is positioned off center and toward one of the lateral sides of the arcuate support frame 104. Although the rail 300 is illustrated in FIG. 11 as one continuous rail, the rail 300 may be embodied as a number of small rails positioned along the length of the top surface 302 of the arcuate support frame 104. The arcuate support frame 104 also includes a number of mounts 304. The mounts 304 are embodied as recessed areas defined on a bottom surface 306 of the arcuate support frame 104. Similar to mounts 120, the mounts 304 are evenly positioned on the bottom surface 306 along the length of the arcuate support frame 104. However, in other embodiments, the mounts 304 may be positioned in any configuration along the length of the arcuate support frame 104.

In such embodiments, the mounting end 122 of the reference array 124 includes a clamp 308 and a mounting base 310. The mounting base 310 is configured to coupled with the rail 300 of the arcuate support frame 104. As such, the mounting base 310 includes a recess 312 configured to receive the rail 300. That is, the recess 312 has dimensions sized such that the rail 300 is able to be received by the recess 312 when the reference array 124 is coupled to the arcuate support frame 104. Similar to the rail 300, the recess 312 is defined in the mounting base 310 toward one of the lateral sides of the base 310. As such, it should be appreciated that the reference array 124 is couplable to the arcuate support frame 104 in a single direction such that the rail 300 is received by the recess 312. In some embodiments, the mounting base 310 may have curved bottom surface 314 corresponding to the curved top surface 302 of the arcuate support frame 104.

The reference array 124 may be coupled to the arcuate support frame 104 at one of the mounts 304. That is, the reference array 124 is coupled to the arcuate support frame 104 such that a pair of prongs 316 of the clamp 308 are received by one of the mounts 304 as illustrated in FIG. 12. The clamp 308 also includes a pair of handles 320, which are biased in an outward direction by a pair of biasing members 322 such that the prongs 316 are in a normally closed position. To couple the reference array 124 to the arcuate support frame 104, a user may depress the handles 320 in an inward direction as indicated by arrows 324 to open the prongs 316. The reference array 124 may then be coupled to the arcuate support frame 104 at any one of the mounts 304 such that the rail 300 is received by the recess 312 of the mounting base 310. When the handles 320 are released, the biasing members 322 bias the handles 320 to an outward position, which causes the prongs 318 to close and be received by the mount 304. As discussed in more detail below in regard to algorithm 200 illustrated in FIG. 16, the reference array 124 may be decoupled from the arcuate support frame 104 and secured to a new mount 304 of the frame 104 at any point during the orthopaedic surgical procedure.

Figure 13:
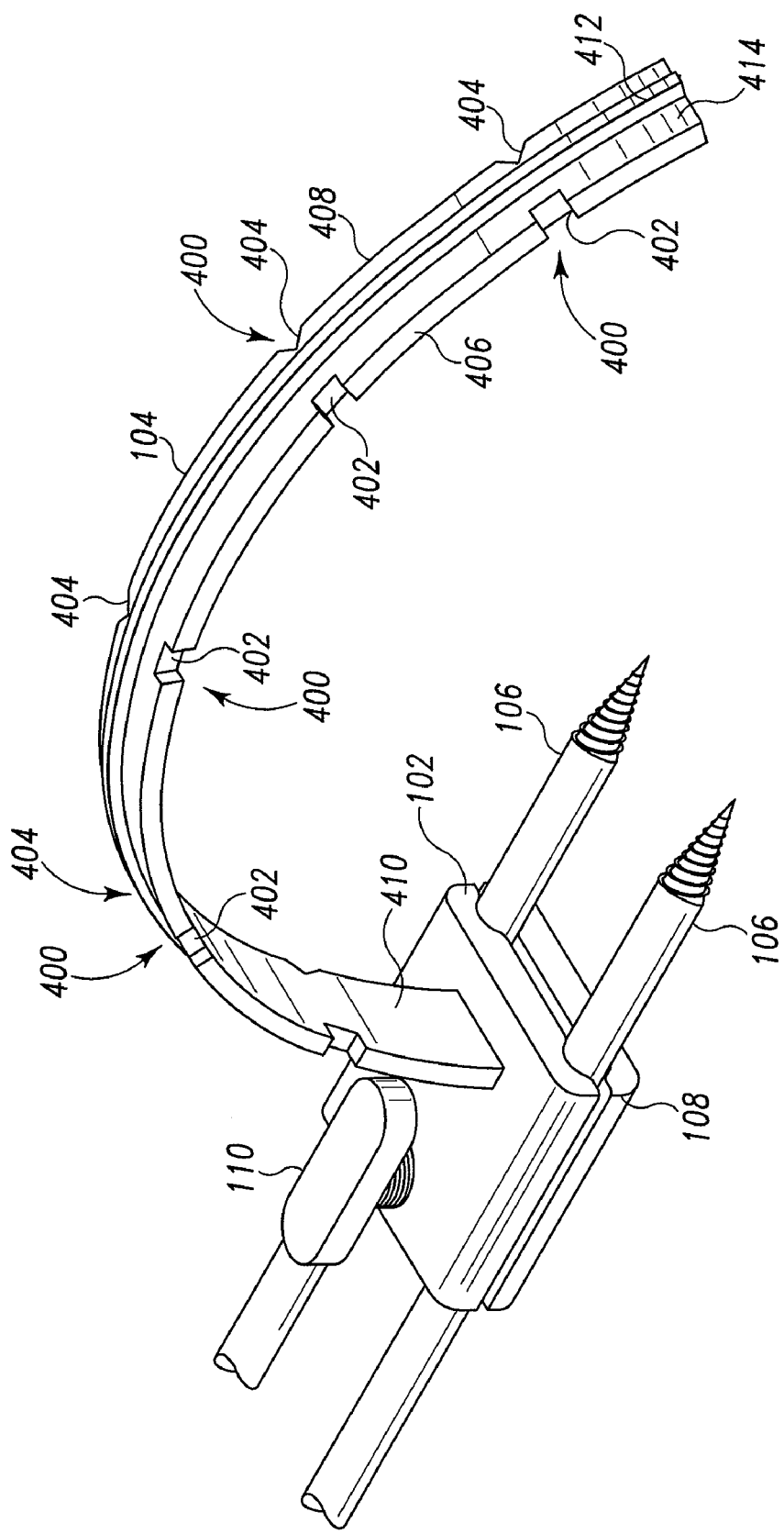
FIG. 13 is a perspective view of yet a further embodiment of the mounting bracket of FIG. 6.

Referring now to FIG. 13, in another embodiment, the arcuate support frame 104 includes a number of mounts 400 evenly positioned on along the length of the arcuate support frame 104. However, similar to the mounts 120, the mounts 400 may be positioned in any configuration along the length of the arcuate support frame 104 in other embodiments. Each of the mounts 400 are embodied as a rectangular recess 402 and a triangular recess 404 defined on the lateral sides 406, 408 of the arcuate support frame 104, respectively. Although the recesses 402, 404 are embodied as rectangular and triangular recesses in the illustrative embodiment, other recess configurations may be used in other embodiments. For example, recesses having semi-circular shape may be used in some embodiments. In some embodiments, each lateral side 406, 408 includes a recess having a geometrical shape different from the recess defined in the opposite lateral side 406, 408. However, in other embodiments, each lateral side 406, 408 may include a recess having a similar geometrical shape to the opposite lateral side 406, 408 but of a different size.

The mounts 400 include different and opposing recesses 402, 404 such that the reference array 124 may be coupled to the arcuate support frame 104 in only a single orientation. In such embodiments, the mounting end 122 of the reference array 124 includes a clamp (not shown) having a pair of prongs configured to be respectively received by the recesses 402, 404. For example, one prong may have a rectangular protrusion configured to be received by one of the recesses 402 while the opposing prong may have a triangular protrusion configured to be received by the recess 404. In addition, when the protrusions of the prongs are received by the recesses 402, 404, the prongs may be configured to wrap around a bottom surface 410 of the arcuate support frame 104 to secure the reference array 124 to the arcuate support frame 104.

In addition, in some embodiments, the arcuate support frame 104 may include a rib 412 defined on a top surface 414. The rib 412 may be centrally located on the top surface 414 or positioned toward one of the lateral sides 406, 408. The rib 412 may extend the length of the top surface 414 of the arcuate support frame 104 or may be embodied as a number of small ribs. In such embodiments, the mounting end 122 of the reference array 124 includes a recess (not shown), similar to recess 312 described above in regard to FIG. 12, configured to receive the rib 412.

Figure 14:
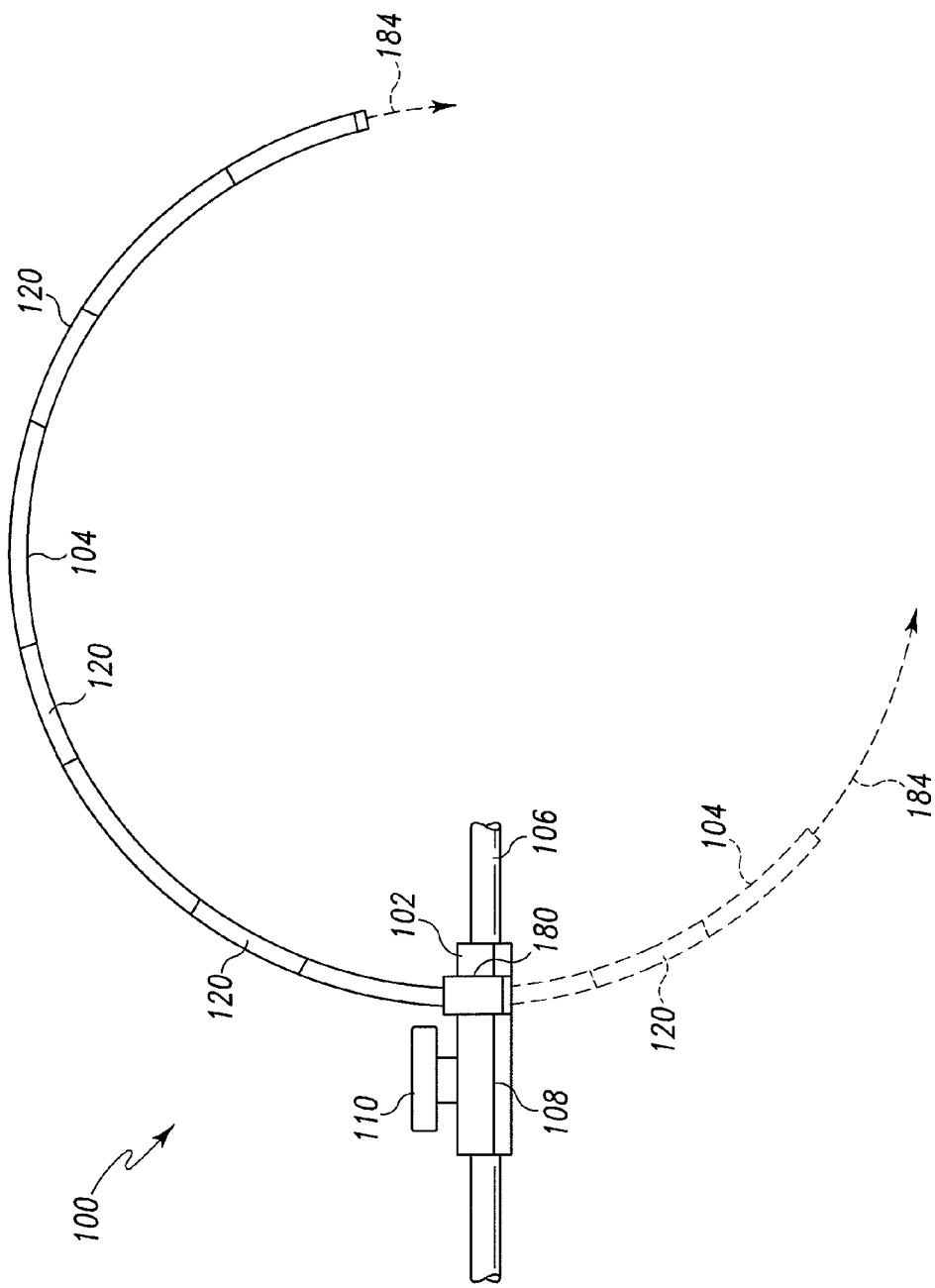
FIG. 14 is a side elevation view of another embodiment of the mounting bracket of FIG. 6.

Referring now to FIG. 14, in another embodiment, the mounting bracket 100 includes a clamp 180 through which the arcuate support frame 104 extends. In such embodiments, the arcuate support frame 104 may be moved with respect to the base 102 along an arc 184 defined by the frame 104. To do so, the arcuate support frame 104 may be slid through the clamp 180. In such embodiments, the clamp 180 or other portion of the bracket 100 may include a locking mechanism (not shown) such that the arcuate support frame 104 may be secured in position after being moved. Once the clamp 180 is locked in this manner, the arcuate support frame 104 is fixed in a location with respect to the base 102. In this way, the arcuate support frame 104 may be rotated or otherwise moved along the arc 184 to a desired position, locked in the desired position, and the reference array 124 may then be coupled to the arcuate support frame 104 without causing the arcuate support frame 104 to pivot from the desired position.

Figure 15:
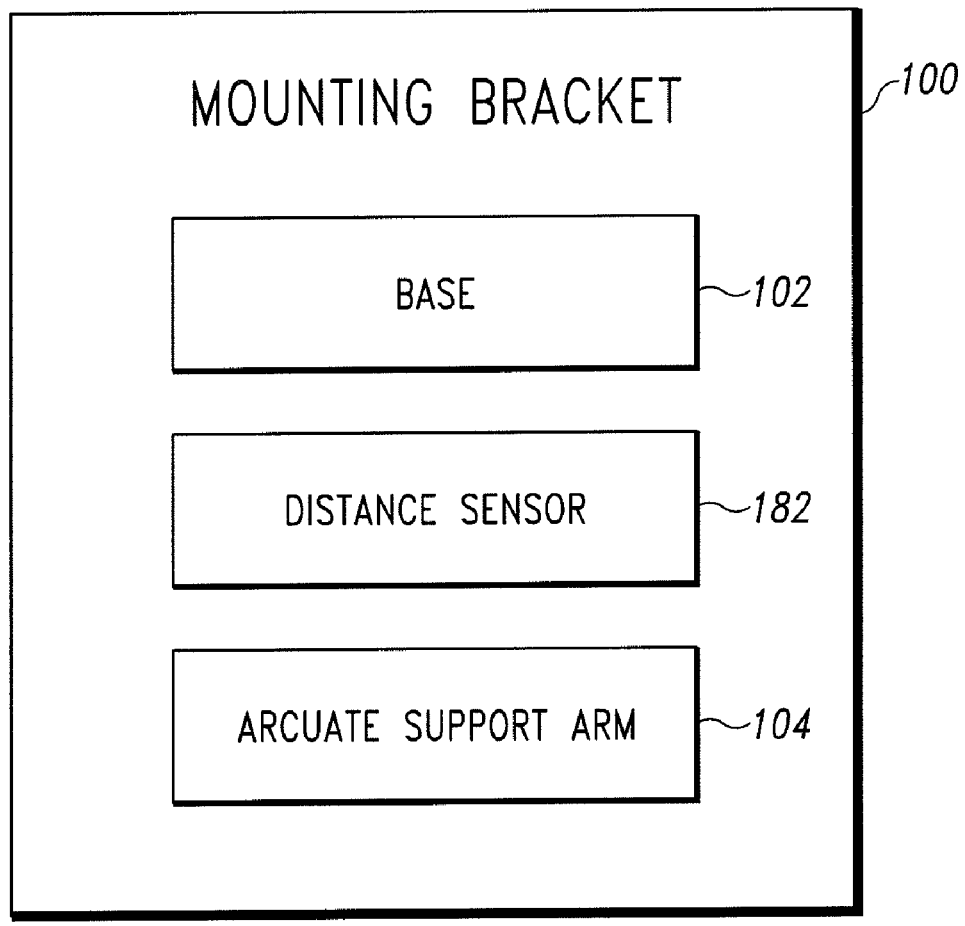
FIG. 15 is a block diagram of the mounting bracket of FIG. 14.

In the embodiment illustrated in FIG. 14, the mounting bracket 100 also includes a distance sensor 182 as illustrated in FIG. 15. The distance sensor 182 is configured to generate a data signal indicative of the distance of the arcuate support frame 104 relative to a predetermined position of the arcuate support frame 104. For example, in one embodiment, the distance sensor 182 is configured to generate data indicative of the arc length distance that the arcuate support frame 104 has been moved from a predetermined reference position. In such embodiments, the distance data generated by the distance sensor 182 is transmitted to the computer 12. To do so, the distance sensor 182 may be communicatively coupled to the computer 12 via a number of communication links such as wires, cables, or the like. Alternatively, the mounting bracket 100 may include a transmitter configured to transmit the distance data from the distance sensor 182 to the computer 12. As discussed in more detail below in regard to FIG. 16, the computer 12 is configured to use the distance data in the determination of the position of the reference array 124 and thereby the bone of the patient 56 to which the mounting bracket 100 is coupled.

Alternatively, in some embodiments, the distance sensor 182 may be replaced with a second reference array coupled to the base 102 similar to reference array 150 illustrated in and described above in regard to FIG. 7. In such embodiments, the computer 12 may be configured to determine the position of the arcuate support frame 104 along the arc 184 by comparing the location of each reference array 124, 150 relative to each other. In this way, the surgeon is not required to instruct the computer 12 as to which position the arcuate support frame is in nor is the distance sensor 182 required to transmit such position data to the computer 12. Additionally, because the position of the arcuate support frame 104 (i.e., the position of the frame 104 along the arc 184) is determined based on the relative positions of the reference arrays 124, 150, the arcuate support frame 104 may be positioned at any location along the arc 184 rather than only at predefined, discrete positions.

Figure 16:
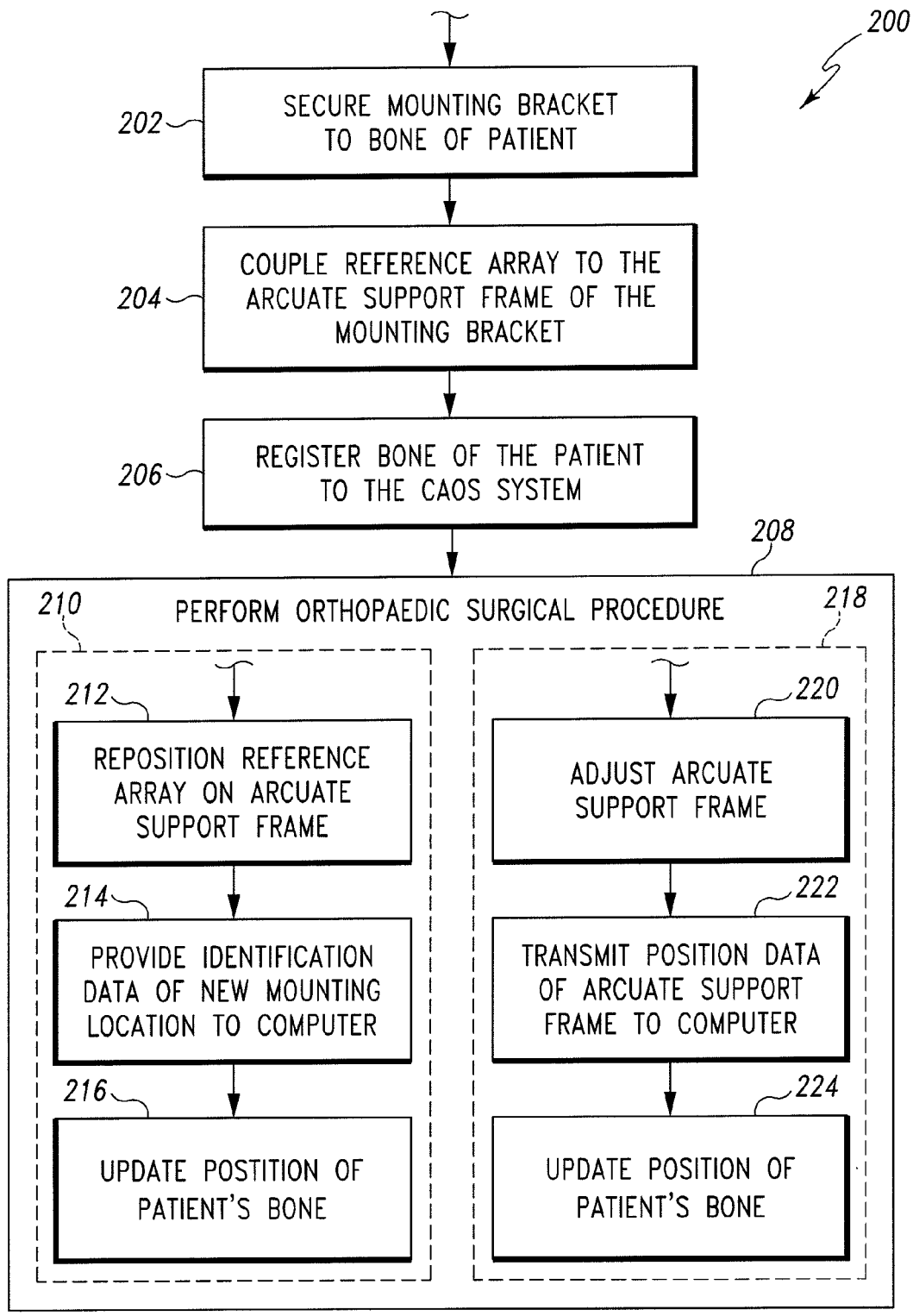
FIG. 16 is an algorithm for operating a computer assisted orthopaedic surgery system.
Figure 17:
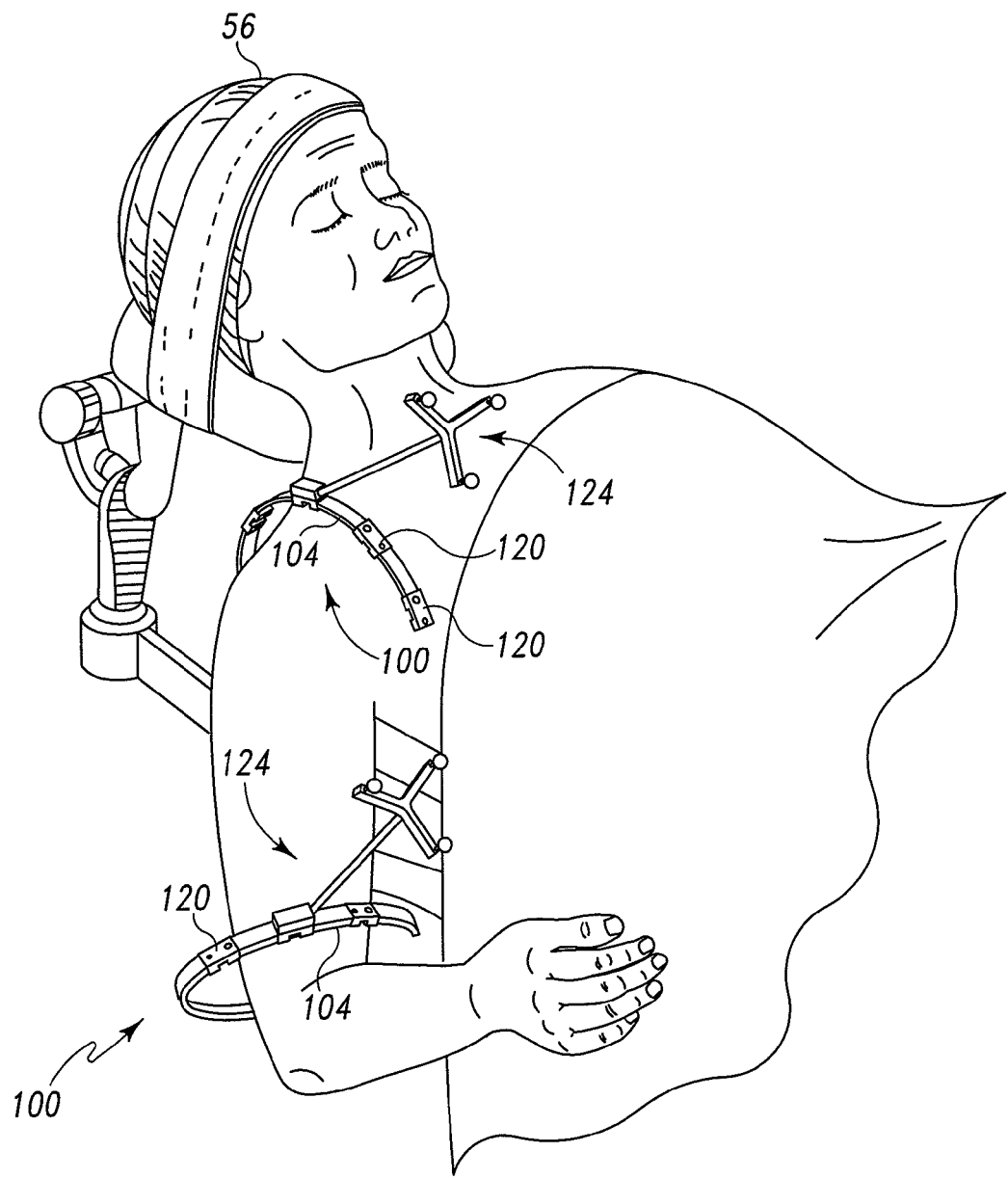
FIG. 17 is a perspective view of the mounting bracket of FIG. 6 coupled to a patient during the performance of an orthopaedic surgical procedure.

Referring now to FIG. 16, an algorithm 200 for operating a computer assisted orthopaedic surgery system begins with process step 202. In process step 202, the mounting bracket 100 is coupled to the desired bone of the patient 56 depending on the particular orthopaedic surgical procedure to be performed. In particular, the mounting bracket 100 may be used in those orthopaedic surgical procedures wherein the relevant bone of the patient 56 will be rotated about a corresponding joint and/or wherein the desirable mounting point of the bone causes a typical reference array to be obscured from view of the camera 24. For example, in a Total Shoulder Arthroplasty surgical procedure, a first mounting bracket 100 may be coupled to the spine of the scapula of the patient 56, which is located toward the back of the patient 56, and a second mounting bracket 100 may be coupled to the humerus of the patient 56 as illustrated in FIG. 17. The mounting bracket(s) 100 is coupled to the relevant bone of the patient 56 via use of the screws 106.

Subsequently, in process step 204, the arcuate support frame 104 is coupled to the mounting bracket 100. The arcuate support frame 104 may be coupled to any one of the mounts 120 of the arcuate support frame 104. To do so, the mounting end 122 of the reference array 124 may be coupled to the desired mount 120 and secured in position via use of the screw 136 as discussed above in regard to FIG. 1. The arcuate support frame 120 may be coupled to any mount 120 that allows the reference array (i.e., the reflective elements 140 of the reference array 124) to be in line-of-sight of the camera unit 16 at the start of the orthopaedic procedure. Because the arcuate support frame 120 has a curved shape, the reference array 124 may be coupled to a mounting position 120 of the arcuate support frame 104 even when base 102 is not visible to the camera unit 16 such as when the mounting bracket 100 is secured to the spine of the scapula of the patient 56 as illustrated in FIG. 17. Additionally, because the arcuate support frame 104 has a number of mounts 120, the reference array 124 may be repositioned during the performance of the orthopaedic surgery if the reference array 124 is not visible or otherwise becomes obscured from the line-of-sight of the camera 24. For example, in embodiments, during a Total Shoulder Arthroplasty surgical procedure, in may be desirable to rotate the humerus of the patient 56. If so, the reference array 124 may be de-coupled from the arcuate support frame 104 and re-coupled to the frame 104 using a new mount 120 such that the reference array 124 is in line-of-sight of the camera 24 while the humerus is in the rotated position as discussed below in more detail.

Next, in process step 206, the bone(s) to which the mounting bracket 100 is coupled is registered with the computer 12. In the registration process, the surgeon 50 supplies data to the computer 12 identifying the mount 120 of the arcuate support frame 104 to which the reference array 124 is coupled. The surgeon 50 may do so by entering data into the computer 12 via an input device such as a keyboard and/or by selecting the appropriate mount 120 via an onscreen menu or the like. The computer 12 is configured to determine the position of the relevant bone based on the position of the reference array 124. That is, data indicative of the structure/configuration of the reference array 124 and the mounting bracket 100 is stored in the computer, for example, in the memory device 42. Based on the location of the reference array 124 and the known structure/configuration of the reference array 124 and the mounting bracket 100, the computer 12 is capable of determine the location and orientation of the relevant bone. In addition, because the mounting bracket 100 has multiple mounts 120, the computer 12 is configured to adjust the determination of the position of the bone based on the particular mount 120 (i.e., based on the data indicative of the mount supplied by the surgeon 56) to which the reference array 124 is coupled.

Subsequently, in process step 208, the orthopaedic surgical procedure is performed. During the orthopaedic surgical procedure, the computer 12 provides surgical navigation to the surgeon 50 by, for example, displaying rendered images of the relevant bone(s) of the patient in a location and orientation determined by the computer 12 as discussed above. As such, the surgeon 50 is able to perform the orthopaedic surgical procedure while monitoring the position of the relevant bones. During the performance of the orthopaedic surgical procedure, it may become necessary to move portions of the patient 56 such as an arm or leg. For example, in a Total Shoulder Arthroplasty surgical procedure, the humerus of the patient 56 is typically rotated up to 180 degrees. When the patient 56 is repositioned in this way, the reference array 124 may become obscured from the line-of-sight of the camera 26. If so, the surgeon 50 may reposition the reference array 124. For example, as shown in sub-algorithm 210, the surgeon 50 may reposition the reference array 124 to a new mount 120 in process step 212. To do so, the surgeon 50 may uncouple the reference array 124 from the arcuate support frame 104 by removing the screw 136. The surgeon may then re-couple the reference array 124 to a new mount 120 such that the reflective elements 140 of the reference array 124 are in the field of view 52 of the camera unit 16 (i.e., are in line-of-sight of the camera 24). The reference array 124 may be secured to the new mount 120 via use of the screw 136.

Next, in process step 214, the surgeon 50 enters identification data of the new mount 120 into the computer 12. The surgeon 50 may enter the identification data into the computer 12 via an input device such as a keyboard and/or by selecting the appropriate mount 120 via an onscreen menu or the like. Once the identification data of the new mount 120 has been entered into the computer 12, the computer 12 is configured to update the position of the rendered image of the patient's bone on the display 44 in process step 216. To do so, the computer 12 determines the position of the patient's bone based on the images of the reference array 124 received from the camera unit 16, the known structure/configuration of the reference array 124 and mounting unit 100, and the identity of the new mount 120. In this way, the surgeon 50 is capable of positioning the patient's 56 body in any configuration while still maintaining the reference array 124 in a line-of-sight relationship with the camera unit 16.

Alternatively or additionally, the arcuate support frame 104 may be repositioned when the reference array 124 becomes obscured from the line-of-sight of the camera unit 16. To do so, as shown in sub-algorithm 218, the surgeon 50 may adjust the arcuate support frame 104 until the reference array 124 is properly positioned in the field of view 52 of the camera unit 16. In embodiments wherein the arcuate support frame 104 is coupled to the base 102 via a hinge 170, as illustrated in FIG. 9, the arcuate support frame 104 may be pivoted to a new position by disengaging the locking mechanism, pivoting the arcuate support frame 104 to the new position, and reengaging the locking mechanism. Alternatively, in embodiments wherein the arcuate support frame 104 is coupled to the base 102 via a clamp 180, as illustrated in FIG. 14, the arcuate support frame 104 may be moved to a new position by disengaging the locking mechanism of the clamp 180, rotating or otherwise moving the arcuate support frame 104 through the clamp 180 to the new position, and reengaging the locking mechanism. Because the reference array 124 is coupled to the arcuate support frame 104, the reference array 124 is also moved to a new position, which is within the line-of-sight of the camera unit 16.

Next, in process step 222, the surgeon 50 position data from the angle sensor 172 and/or the distance sensor 182 is transmitted to the computer 12. Once the position data has been transmitted has been received by the computer 12, the computer 12 is configured to update the position of the rendered image of the patient's bone on the display 44 in process step 224. To do so, the computer 12 determines the position of the patient's bone based on the images of the reference array 124 received from the camera unit 16, the known structure/configuration of the reference array 124 and mounting unit 100, and the position data indicative of the position of the arcuate support frame 104 received from the angle sensor 172 and/or the distance sensor 182. In this way, the surgeon 50 is capable of positioning the patient's 56 body in any configuration while still maintaining the reference array 124 in a line-of-sight relationship with the camera unit 16.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the systems, devices, and methods described herein. It will be noted that alternative embodiments of the systems and methods of the present disclosure may not include all of the features described yet still benefit from at least some of the advantages of such features. Those of ordinary skill in the art may readily devise their own implementations of the systems, devices, and methods that incorporate one or more of the features of the present invention and fall within the spirit and scope of the present disclosure as defined by the appended claims.

The invention claimed is:

1. A reference array assembly for use with a computer assisted surgery system, the reference array assembly comprising:
 a reference array having a mounting end;
 a mounting bracket configured to be coupled to a bone of a patient, the mounting bracket including a base and an arcuate support frame pivotably coupled to the base, the arcuate support frame having a plurality of mounts, each of the plurality of mounts being configured to be coupled to the mounting end of the reference array such that the mounting end of the reference array is coupled to a single mount of any of the plurality of mounts; and
 an angle sensor configured to generate angle data and provide the computer assisted surgery system with angle data indicative of an angle defined between the base and the arcuate support frame.

2. The reference array assembly of claim 1, wherein the arcuate support frame includes an outer curved surface, an inner curved surface, and a rib support defined on the inner curved surface.

3. The reference array assembly of claim 1, wherein the arcuate support frame includes an outer curved surface, an inner curved surface, and a rib support defined on the outer curved surface.

4. The reference array assembly of claim 1, wherein the arcuate support frame comprises a rail defined on a top surface, wherein the rail extends in an upwardly direction from the top surface of the arcuate support frame.

5. The reference array assembly of claim 1, wherein each of the mounts comprises a first recess defined in a first lateral side of the mount and a second recess defined in a second lateral side of the mount, the first recess having a geometric shape different from the second recess.

6. The reference array assembly of claim 1, wherein the arcuate support frame subtends an angle of 90 degrees to 180 degrees.

7. The reference array assembly of claim 1, wherein the arcuate support frame is movable with respect to the base about an arc defined by the arcuate support frame.

8. The reference array assembly of claim 7, further comprising a distance sensor configured to generate data indicative of the distance of the arcuate support frame along the arc with respect to a predetermined position of the arcuate support frame.

9. The reference array assembly of claim 1, further comprising a second reference array coupled to a base of the mounting bracket.

10. The reference array assembly of claim 1, wherein the mounting bracket is sterile.

11. A computer assisted orthopaedic surgery system comprising:
 a first reference array having a mounting end;
 a mounting bracket configured to be coupled to a bone of a patient, the mounting bracket including a base, an arcuate support frame coupled to the base, and an angle sensor configured to generate angle data indicative of an angle defined between the base and the arcuate support frame, the arcuate support frame having a plurality of mounts, each of the plurality of mounts being configured to be coupled to the mounting end of the first reference array such that the mounting end of the first reference array is coupled to a single mount of any of the plurality of mounts; and
 a computer configured to determine the position of the bone of the patient based on a position of the first reference array and the angle data.

12. The computer assisted orthopaedic surgery system of claim 11, wherein:
 the mounting bracket comprises a distance sensor configured to generate distance data indicative of the distance of the arcuate support frame along an arcuate path defined by the arcuate support frame with respect to a predetermined position of the arcuate support frame, and
 the computer is configured to determine the position of the bone of the patient based on the distance data.

13. The computer assisted orthopaedic surgery system of claim 11, further comprising a second reference array, wherein:

the mounting bracket includes a base configured to be coupled to the bone of the patient and to the second reference array, and the computer is configured to determine the position of the bone of the patient based on the position of the first reference array relative to second reference array.

14. A reference array assembly for use with a computer assisted surgery system, the reference array assembly comprising:

a reference array having a mounting end; and a mounting bracket configured to be coupled to a bone of a patient, the mounting bracket including an arcuate support frame and a distance sensor configured to generate distance data indicative of the distance of the arcuate support frame along an arcuate path defined by the arcuate support frame with respect to a predetermined position of the arcuate support frame and to provide the distance data to the computer assisted surgery system, the arcuate support frame comprising (i) an outer curved surface, (ii) an inner curved surface, (iii) a plurality of mounts, and (iv) a plurality of rib supports;

wherein each of the plurality of mounts is configured to be coupled to the mounting end of the reference array such that the mounting end of the reference array is coupled to a single mount of the plurality of mounts, and wherein each of the plurality of rib supports is defined between a different pair of mounts of the plurality of mounts.

15. The reference array assembly of claim 14, wherein each of the plurality of rib supports is defined on the inner curved surface of the arcuate support frame.

16. The reference array assembly of claim 14, wherein each of the plurality of rib supports is defined on the outer curved surface of the arcuate support frame.

17. The reference array assembly of claim 14, wherein the mounting bracket further comprises a base and a hinge, wherein the base is pivotably coupled to a first end of the arcuate support frame with the hinge, and a second end of the arcuate support frame is detached from the base.

18. The reference array assembly of claim 14, wherein each mount of the plurality of mounts comprises a first aperture defined in a first lateral side of the mount and a second aperture defined in a second lateral side of the mount, the first aperture having a diameter different from the second aperture.

* * * * *

UNITED STATES PATENT AND TRADEMARK OFFICE
CERTIFICATE OF CORRECTION

| | |
|---|---|
| PATENT NO. | : 8,357,165 B2 |
| APPLICATION NO. | : 11/946445 |
| DATED | : January 22, 2013 |
| INVENTOR(S) | : Stuart Grant and Daren L. Deffenbaugh |

It is certified that error appears in the above-identified patent and that said Letters Patent is hereby corrected as shown below:

On the title page, item [75], the inventor's name reading "Darren L. Deffenbaugh" should read --Daren L. Deffenbaugh--.

Signed and Sealed this
Twenty-third Day of July, 2013

Teresa Stanek Rea
*Acting Director of the United States Patent and Trademark Office*